United States Patent [19]

Shettigar

[11] Patent Number: 5,055,198
[45] Date of Patent: Oct. 8, 1991

[54] AUTOLOGOUS BLOOD RECOVERY MEMBRANE SYSTEM AND METHOD

[76] Inventor: U. Ramakrishna Shettigar, 1324 Medical Plz., Salt Lake City, Utah 84112

[21] Appl. No.: 525,536

[22] Filed: May 18, 1990

Related U.S. Application Data

[63] Continuation-in-part of Ser. No. 491,183, Mar. 7, 1990, abandoned.

[51] Int. Cl.[5] .............................................. A61M 1/03
[52] U.S. Cl. .................................... 210/650; 210/104;
210/136; 210/257.2; 210/258; 210/259;
210/314; 210/321.6; 210/406; 210/416.1;
210/472; 210/744; 210/806; 210/808; 604/4;
604/28; 604/35; 604/36; 604/319; 604/404;
604/406
[58] Field of Search ............... 210/650, 744, 806, 86,
210/97, 104, 136, 257.2, 258, 259, 295, 299, 314,
321.6, 321.82-321.9, 772, 805, 808, 406, 416.1,
472; 604/4, 5, 6, 28, 35, 36, 317, 318, 319, 320,
321, 404, 406

[56] References Cited

U.S. PATENT DOCUMENTS

| | | | |
|---|---|---|---|
| 2,804,075 | 8/1957 | Borden | 604/269 |
| 3,896,733 | 7/1975 | Rosenberg | 604/4 |
| 3,965,896 | 6/1976 | Swank | 604/4 |
| 3,993,067 | 11/1976 | Schachet et al. | 604/4 |
| 4,006,745 | 2/1977 | Sorenson et al. | 604/4 |
| 4,014,329 | 3/1977 | Welch et al. | 604/4 |
| 4,033,345 | 7/1977 | Sorenson et al. | 604/4 |
| 4,047,526 | 9/1977 | Reynolds et al. | 604/4 |
| 4,631,050 | 12/1986 | Reed et al. | 604/4 |
| 4,744,785 | 5/1988 | Rosenthal et al. | 604/319 |
| 4,772,256 | 9/1988 | Lane et al. | 604/4 |
| 4,796,644 | 1/1989 | Polaschegg | 604/4 |
| 4,798,578 | 1/1989 | Ranford | 604/4 |
| 4,867,738 | 9/1989 | Mintz | 604/4 |
| 4,874,359 | 10/1989 | White et al. | 604/4 |
| 4,886,487 | 12/1989 | Solem et al. | 604/5 |
| 4,898,572 | 2/1990 | Surugue Nee Lasnier et al. | 604/4 |
| 4,976,682 | 12/1990 | Lane et al. | 604/4 |

Primary Examiner—W. Gary Jones
Attorney, Agent, or Firm—Trask, Britt & Rossa

[57] ABSTRACT

An apparatus for recycling autologous blood from a patient for reinfusion back to the patient comprising suction means, admixing means for admixing aspirated blood with a washing fluid, filtering means for filtering the admixture through an emboli filter and a membrane filter, monitoring means for measuring the amount of cellular component volume in the filtered blood, filtration means for removing excess fluid and particulates from the blood, and reinfusion means is disclosed. Embodiments for use during surgery for on-line purification and reinfusion on a real time basis are disclosed along with embodiments for use post-surgically when the wound site is closed and drainage tubing has been implanted at the wound site to draw off blood post-surgically. Methods for performing the autotransfusion process are also disclosed.

64 Claims, 13 Drawing Sheets

AUTOLOGOUS BLOOD RECOVERY MEMBRANE SYSTEM AND METHOD

RELATED APPLICATION

This application is a continuation-in-part of applicant's copending application Ser. No. 491,183 filed Mar. 7, 1990, now abandoned, the contents of which are incorporated by this reference.

BACKGROUND

1. Field of the Invention

The present invention pertains to methods and apparatus for recovery, purification and reinfusion of blood lost at a wound site, either during a surgical or postsurgical management period. More specifically, the present invention applies to aspiration of shed blood from a wound site during intraoperative or postsurgical recovery periods, on-line purification of aspirated blood by filtration and cell-washing using membranes, and reinfusion of purified autologous blood to the patient on a real time basis. With some modifications, the present invention may be used as a hemofiltration or ultrafiltration system for the treatment of acute and end-stage renal diseases.

2. Statement of the Art

Significant blood loss to a person may occur during a traumatic injury, such as an auto accident, or during a serious and traumatic surgery, such as open heart surgery, or during a postsurgical recovery period due to hemorrhagic conditions. Significant loss in blood results in decreased blood pressure, decreased cardiac output, and decreased oxygen delivery to tissues, particularly brain cells. For these reasons, it is necessary to compensate the loss in blood by transfusing the patient with blood as soon as possible.

During an intraoperative period, a pool of shed blood accumulates in the wound site which obstructs the surgery site unless it is aspirated out therefrom. Usually, suction is provided to remove the shed blood, other accumulated fluids, blood clots and other tissue debris. The total loss of blood may vary from 1,000 ml to 15,000 ml depending on the extent of the surgery and the attendant traumatic conditions.

During a postsurgical recovery period due to hemorrhagic conditions, the closed wound may continue to bleed into the chest, pleural cavity, or abdominal cavity. On an average, 1,000 ml of blood is usually lost over a five hour period. However, blood loss could conceivably be as high as 21,350 ml. In such instances, the patient may have to be rushed back to surgery to correct the underlying problem. It is obvious that blood transfusion is imperative under such conditions. Usually, the shed blood is drained from the body cavity using drainage tubing under a controlled suction. The drained blood is generally collected in a container.

Blood shed during intraoperative or postsurgical recovery periods can be collected in a container and reinfused to the patient provided the salvaged blood is free of impurities. Typical impurities are blood clots, tissue debris, hair, foreign particles, activated coagulation factors, denatured proteins, plasma free hemoglobin, and any other fluids (e.g. irrigation fluid) that are being introduced into the wound site by medical personnel.

Impurities in salvaged blood are conventionally filtered out using a 40 micron filter to remove particles greater than 40 microns in size, and the blood is then subjected to "cell washing." The cell washing technique may involve mixing blood with a physiological solution (e.g., saline or Ringer's) in equal proportion to the blood. The blood is then centrifuged to recover the heavier blood cells which are suitable for reinfusion to the patient. The lighter portion of the centrifuged fluid (i.e., the top portion of the centrifuge tube content) containing platelets, white cells, plasma proteins and antibodies is usually discarded as waste. This is a significant loss to the patient, particularly the loss of coagulation factors, platelets, white cells and antibodies. Therefore, the efficiency of recovery of blood products by conventional cell washing techniques is low. Additionally, conventional blood recovery methods are not accomplished on-line, and in real time. Rather, they are batch processes involving operator intervention, and are subject to human errors and time delay.

Thus it will be appreciated that purification of salvaged blood based on cell-centrifuge machines are not designed to work on a real time basis. That is, there is considerable lag time (more than 15 minutes) between the moment of aspiration of blood and reinfusion of processed autologous blood. This is a significant problem, especially when the patient bleeds rapidly, and his/her lost blood volume needs to be compensated immediately. Furthermore, during cell washing by the centrifuge technique, a significant amount of red blood cells are lost, and almost all white blood cells, platelets and plasma proteins including antibodies.

Due to the aforementioned problems in the conventional cell washing technique, a patient is usually given homologous (donor) blood transfusions rather than his/her own blood, which is still being processed.

Problems with homologous blood transfusion are many. The major problem is providing suitable donor blood which will not cause side effects, such as anaphylactic reactions, and which does not contain donor-associated infections, such as hepatitis, malaria, or acquired immune deficiency syndrome (AIDS). At times, it is difficult to find appropriate types and amounts of blood necessary for transfusions, and it can become very expensive.

Due to the aforementioned problems, "autotransfusion" (reuse of a patient's own blood) has received significant attention. A number of autotransfusion systems have been developed in recent years with varying system configurations. They are composed of three basic units; an aspirator unit, a cell washing unit, and a reinfusion unit.

The typical aspirator unit consists of a suction handle attached to suction tubing which is connected to an emboli filter reservoir. The emboli filter is generally provided with an air vent line, a degassifier, a filter, and a blood reservoir. Controlled suction is usually applied with a vacuum source via a vent line. The vacuum aspirates shed blood, along with other impurities, from the wound site. Larger impurities are trapped in the emboli filter.

Filtered blood is usually pumped to a cell centrifuge machine where it is mixed with an appropriate "washing fluid" and centrifuged for a specified time period until the heavier blood cells are separated from the plasma. This method is typically cumbersome, time consuming, and requires an operator to attend to the system continuously. Furthermore, there is a loss of precious plasma proteins, antibodies, and white blood cells which are important for the body's ability to fight infection. Thus, it would be an advancement in the art to provide on-line, continuous methods and apparatus for blood purification which would minimize loss of precious blood elements, and would reinfuse to the patient his/her own blood on a real time basis. It would be a further advancement to provide an automatic system which would reinfuse whole blood at a specified hematocrit level free of air emboli.

The aforementioned prior art systems are designed to be used during surgery (i.e., intraoperative period). During the post-surgical recovery period, bleeding may still continue from the closed wound, but at a significantly reduced flow rate. Bleeding usually progresses at about 1,000 ml over a five hour period. Post-surgical autotransfusion of shed blood is particularly useful in postoperative management of patients with serious hemorrhage. Post-surgical blood losses may range from 2,050 ml to 21,350 ml. The shed blood is usually drained using a drainage unit by a controlled suction.

There are many chest drainage units on the market. Examples are the "Pleur-evac" chest drainage unit by Deknatel, Howmedica, Inc., New York; "Sentinel Seal Compact" "chest drainage unit" by Argyle; "Snyder Hemovac Compact Evacuator", Zimmer Corp., Dover, Ohio; and "Sorenson Autotransfusion System", Salt Lake City, Utah. In all these drainage units, a controlled suction (i.e., where negative pressure does not exceed $-25$ Cm of water) is applied to drain the shed blood from the closed wound site via one or two drainage tube. The drained blood is filtered to remove solid particulates and is collected in a bag. When a suitable volume of blood is collected, it can be reinfused to the patient directly without washing the blood cells, or it can be reinfused to the patient after it is washed with saline solution using a cell centrifuge machine. A 40 micron filter (e,g., a "Pall filter") is typically used during reinfusion of the blood. Care is taken to protect the closed wound from excessive negative pressure (e.g., greater than $-20$ Cm water), and to minimize the blood-air interface.

None of the aforementioned systems wash the blood on-line; rather, the washing needs to be done in a batch operation using a cell centrifuge. Since a controlled suction is applied to the drainage tubing using a vacuum pump, the blood-air interface is not completely eliminated in those systems. Thus, it would be an advancement in the art to provide an automatic post-surgical autotransfusion system which eliminates the problems described above.

SUMMARY OF THE INVENTION

The invention is generally directed to the filtration and processing of blood aspirated from a patient, either during or after surgery, for ultimate reinfusion into the patient. The invention generally includes means for aspirating blood from the wound site, means for admixing a washing fluid with the aspirated blood, means for filtering air emboli, particulate matter, unwanted impurities, and excess fluid from the blood, and means for reinfusion of the purified blood into the patient.

Embodiments of the invention are directed to use during a surgical procedure when the wound site is open, and other embodiments of the invention are directed to use during postsurgical recovery for draining blood which may be lost from a closed wound site as a result of hemorrhage conditions.

Blood is aspirated from a wound site by suction means which may typically include a suction tip and handle for directing the tip into the wound site. Suction is accomplished by attachment of a vacuum source to the system which applies a negative pressure of up to $-200$ mm Hg. Washing fluid, which is retained in a suitable retainer means, is mixed with the aspirated blood. The washing fluid retainer means may be either a collapsible bag, a non-collapsible bag, or a similarly suitable retainer. The washing fluid may be any type of conventional fluid used in surgery, such as normal saline or Ringer's solution, and may contain an appropriate anticoagulant substance, such as heparin. The washing solution, which aids in removal of impurities, is admixed with the aspirated blood in approximate proportion to the amount of blood aspirated.

Washing fluid admixed with aspirated blood aids in purifying the blood of impurities. Therefore, it is desirable that washing fluid be introduced into the aspirated blood in approximately equal proportion thereto. The admixture of equal proportions of blood and washing fluid could be accomplished by use of sophisticated machinery. However, in the interest of simplicity, some embodiments of the invention employ a novel method of attaining equal proportions of blood and washing fluid. The embodiments are configured so that the washing fluid retainer is approximately two feet below the height of the suction means. When blood is aspirated into the system, it causes the negative pressure applied to the system to increase. The increase in negative pressure results in the increase of negative pressure acting upon the washing fluid retainer, and washing fluid is thereby urged into the system in proportion to the amount of blood being aspirated. Conversely, when no blood is being aspirated, the negative pressure created by the vacuum in the suction means is too low to draw any washing fluid into the system. The flow resistance of blood being aspirated into, or conducted through, the system is influenced by the diameter of tubing used. Therefore, the size of tubing used in the system should be from about 4 mm to about 10 mm in diameter.

The present invention provides a continuous on-line method of removing air, impurities, unwanted cellular and blood components, and excess fluid. The blood and washing fluid admixture is directed through an emboli filter which traps and removes air bubbles from the admixture. The emboli filter is also capable of trapping particulate matter of relatively large size. An emboli filter has been especially designed to enhance the separation of particulates and air bubbles from the aspirated blood and washing fluid admixture.

The blood and washing fluid admixture is also directed through a membrane filter, which may be an ultrafilter or a plasma filter, which removes smaller impurities along with excess fluid. The unwanted components and excess fluids which are filtered from the blood is drawn off into filtrate retention means. In some embodiments of the invention, the blood is continuously recirculated through the filtering system until a sufficient amount of fluid has been removed and a specified level of desired blood components (i.e., hematocrit level) has been attained. This is determined by monitoring means associated with the apparatus. Recirculation may be accomplished by mechanical means, such as a roller pump, or may be accomplished manually by, for example, applying alternating force or pressure which may force the admixture to pass through the filter means continuously. When the blood component portion of the blood has reached a specified level, the blood is reinfused into the patient. The specific level of desired blood components, or the hematocrit level, will be determined by the attending medical personnel.

In alternative embodiments, the blood is not recirculated. Rather, the blood is passed through an integrated emboli filter and membrane filter. When sufficient amounts of excess fluid have been removed, as measured by monitoring means, the filtered blood is ready for reinfusion into the patient.

The monitoring means for use in this system may be any means which determines the amount of fluid in the blood being circulated through the system. For example, such a monitor may constantly monitor the fraction of noncellular fluid volume in the blood by measuring the impedance of blood at a specified frequency using two stainless steel electrodes located in proximity to the filter means. Measured conductivity of blood is known to be proportional to the fraction of noncellular fluid volume in the blood. Such conductivity monitors are available on the market (e.g., Sedatelec, Chemin des Muriers, Irigny, France).

In an alternative embodiment of the invention, a further filter, similar to the emboli filter of the system, is associated with the reinfusion system and operates to remove any residual air bubbles before the blood is reinfused.

Membrane filters which can be used in the invention to purify blood are those which have the capability of trapping unwanted impurities of a particular size. For example, an ultrafilter may be used which is a conventional membrane separator having a pore size ranging from about 40,000 daltons to about 400,000 daltons molecular weight cut off. A preferred pore size is about 100,000 daltons. Representative filters are ultrafilters manufactured by the Kuraray Company of Japan. However, if larger impurities are to be removed, a plasma filter having a pore size larger than about 400,000 daltons, and up to 0.4 microns, may be preferred.

Blood which has been filtered, and which comprises appropriate levels of blood cellular components and fluid, is collected in blood collection means. The blood collection means may be a collapsible bag or a rigid, non-collapsible bag. The invention, whether highly mechanized or simplistically configured, is designed to process blood on a real-time basis. The filtered blood may be collected in a bag and reinfused by a batch-type process, or the collected blood may be constantly reinfused from the apparatus of the invention. If collected by batch processing, the filtered blood may be collected in a bag and may be attached, for example, to an I.V. pole for reinfusion. Alternatively, the blood may be infused continuously to the patient from a reinfusion line connected to the blood collection means of the system.

The invention may be configured as a stand-alone unit which can, for example, be wheeled into the operating forum or intensive care unit following surgery. Alternatively, the invention may be configured as a portable system attached to a conventional I.V. pole.

Embodiments of the invention employ varying degrees of mechanization to accomplish the different steps of blood aspiration and filtration. Those systems which are less mechanized are preferred embodiments since they allow easier handling, are less dependent on mechanical and electrical components which may fail, and are ultimately less expensive. One embodiment of the invention, for example, presents a "machineless" means of filtering blood. That is, it uses the force of gravity to accomplish filtration of aspirated blood and washing fluid through the membrane filter, and to drain filtrate (waste). Gravity and manipulation of negative pressure applied to the system effectuates recirculation of the admixed blood and washing fluid through the membrane filter for filtering. Thus, aspiration and filtration of the blood through this, the simplest of embodiments, is accomplished with no collateral machinery other than a vacuum source.

Other embodiments may employ pumps, such as roller pumps, to provide movement to the circulating admixture in the system, and to provide slight pressure at various points. For example, pumps may be used to infuse washing fluid into the system for admixture with the aspirated blood, to aid in drainage of filtrate from the membrane filter, to aid in reinfusion, and to cause recirculation of the blood and washing fluid admixture through the system.

In a more mechanized embodiment, a series of pumps, valves, and blood level detectors may be in electrical or mechanical communication with each other such that processing of the blood is fully automated. In some embodiments, for example, aspirated blood is filtered through an emboli filter and collects temporarily in a reservoir associated with the emboli filter. Blood level detectors connected to the reservoir measure a high level of blood in the reservoir and a low level of blood in the reservoir. The blood level detectors may be ultrasonic bubble detectors which detect the presence of air in the system, thereby signalling when blood level has dropped. A signal is thus communicated to a recirculation pump when the blood level is high in the reservoir, causing the pump to pump faster. Correspondingly, a signal is sent to the recirculation pump when the level of blood gets too low in the reservoir, and the recirculation pump slows or stops.

As the blood/washing fluid admixture circulates through a membrane filter, fluid and other waste components are removed. Removal of the filtrate may be increased by a filtration pump associated with the filtrate drainage means. As the filtered blood exits the membrane filter, a monitor determines the amount of fluid and desired blood components in the blood. If there is an excess of fluid still remaining in the blood, the recirculation continues. However, when the proper amount of fluid has been removed, as determined by the monitor, a signal is sent to a shunting valve which closes off the pathway to recirculation, and opens the pathway to reinfusion. The blood is filtered once more of air bubbles and monitored. If no air bubbles exist, a signal is sent from the detector to a reinfusion valve which then opens, allowing the filtered blood to be reinfused into the patient. The reinfusion valve may also be in communication with the blood level detectors of the reservoir such that if the blood level in the reservoir is too low, the reinfusion valve will not open.

The invention may be used during surgery or postsurgically. Embodiments for postsurgical use provide a method of controlled negative pressure in the drainage tubing, which is implanted in the closed wound site and is used to drain blood from the area. By controlling the negative pressure in the drainage tubing, blood may be aspirated without introduction of air into the system. This has the obvious advantage of reducing air emboli, and it further lessens protein denaturation as a result. Postsurgical embodiments may be mechanized to varying degrees, as discussed above, or may be fairly simple and manually operated. Such embodiments are easy to handle, are less expensive, and are less subject to mechanical failure.

The embodiments of the invention may be more clearly understood from the drawings and description which follow.

BRIEF DESCRIPTION OF THE DRAWINGS

FIG. 8-B is a cross-sectional view of a spring-loaded piston system which may be used with the embodiment illustrated in FIG. 8-A to regulate the vacuum pressure;

DETAILED DESCRIPTION OF THE DRAWINGS

Figure 1:
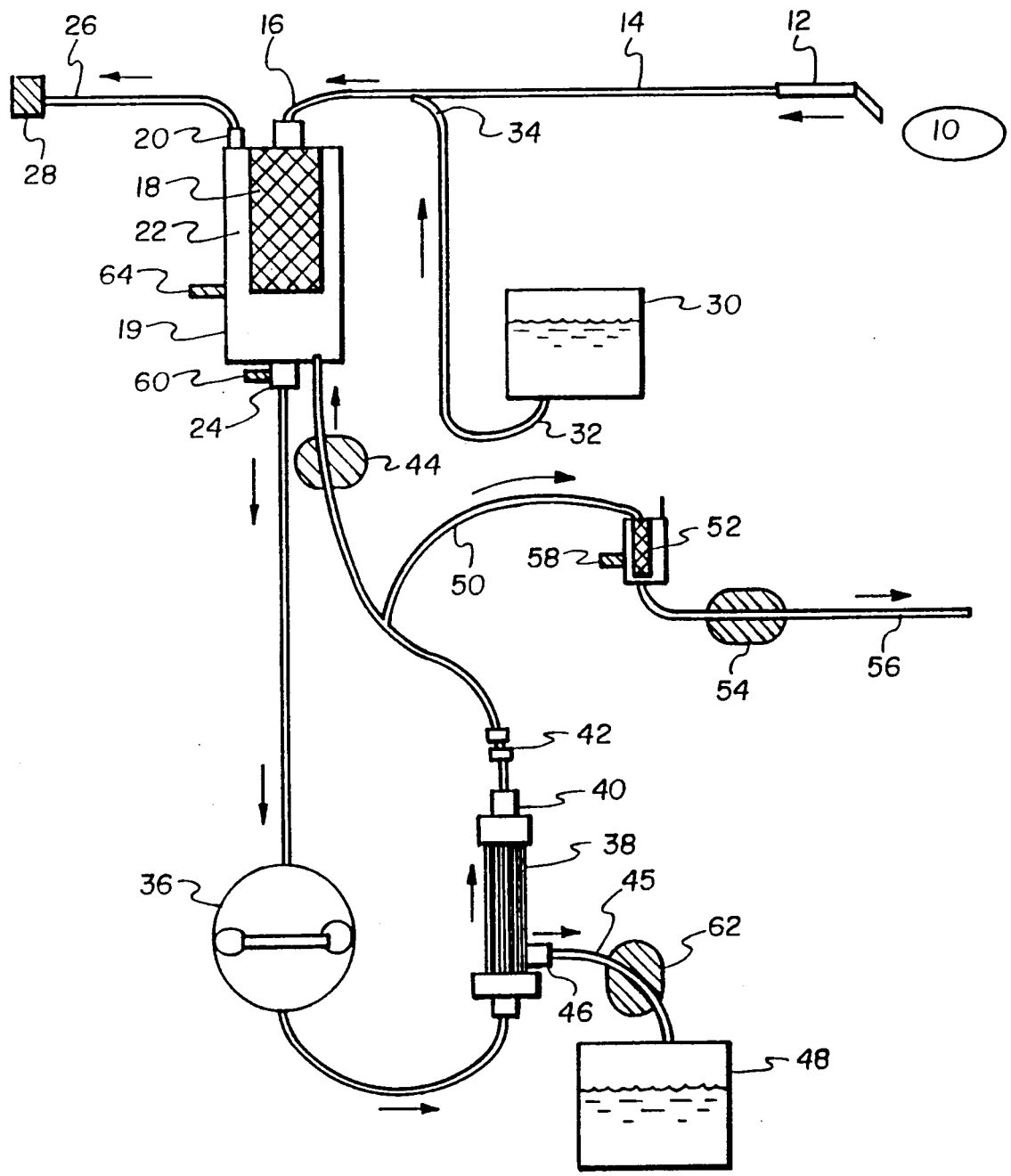
FIG. 1 is a schematic diagram illustrating an embodiment of the invention which is an intraoperative autotransfusion system.

FIG. 1 illustrates an embodiment of the invention for use during surgery. In FIG. 1, the location of the wound site is designated generally at 10. The wound site could be a surgically-induced wound or a serious trauma resulting from an accident, such as a gun-shot wound.

When there is bleeding at the wound site 10, the shed blood is aspirated by suction means 12. The suction means 12 generally includes a handle and a suction tip. The suction means 12 is connected to suction tubing 14. The other end of the suction tubing is connected to the blood inlet port 16 of an emboli filter 18 or cardiotomy reservoir. The emboli filter 18 is enclosed within an emboli filter casing 19. The emboli filter casing is provided with a vacuum connector means 20 near the top of the casing 19. Space between the emboli filter casing 19 and the emboli filter 18 forms a blood reservoir 22. An aperture in the bottom of the emboli filter casing 19 opening into the reservoir 22 forms blood outlet 24. To the vacuum connector means 20 is connected a vent line 26 which may be connected to a controlled vacuum source 28. Most operating rooms are generally equipped with a vacuum source which can be controlled at any desired value.

The invention provides a method of delivering washing fluid to be mixed with the aspirated blood at a rate in proportion to the flow rate of the aspirated blood. A bag or retainer 30 containing washing fluid is located from about equal in height to the suction means 12 to about two feet below the suction means 12. A washing fluid line 32 extending from the washing fluid bag 30 is connected to the suction tubing 14 by a Y-connector 34. The washing fluid bag is a conventional collapsible plastic bag used for fluid retention. The washing fluid may be any physiological fluid such as normal saline or Ringer's solution. The washing fluid may be mixed with an anticoagulant, such as heparin, in order to prevent clotting of blood in the autotransfusion system.

When there is no bleeding in the wound site 10, the suction means 12 is not exposed to blood and remains open to the atmosphere. During this period, air sucked into the suction tubing 14 flows into the emboli filter 18, and is then removed through the vacuum connector means 20 via the vent line 26. Due to the aspiration of air through the suction means 12, which offers a very low resistance to flow, the negative pressure in the suction tubing 14 decreases to almost the level of atmospheric pressure. This decreased negative pressure in the suction tubing 14 will not be sufficient to lift the washing fluid from the washing fluid bag 30 into the washing fluid line 32. In other words, when there is no bleeding, the washing fluid flow rate reduces to zero.

It will be appreciated that by suitably adjusting the flow resistance in the washing fluid line 32 with respect to the flow resistance in the suction tubing 14 and suction means 12, the flow rate of washing fluid may be regulated at any desired value. Such resistance may be achieved by varying the diameter of the washing fluid line 32.

When there is bleeding, the suction means 12 is inserted in the pool of blood to remove it from the wound site in order to keep the wound site clear for surgery. Due to the application of vacuum in the suction tubing 14, the aspirated blood is transported from the wound site 10 into the emboli filter 18 through the suction tubing 14. This increases the flow resistance in the suction tubing 14, which increases the negative pressure in the washing fluid line 32. Increased negative pressure is then sufficient to lift the washing fluid from the bag 30. The washing fluid will then flow into the suction tubing 14 through the Y-connector 34 where it is mixed with the aspirated blood.

Figure 9:
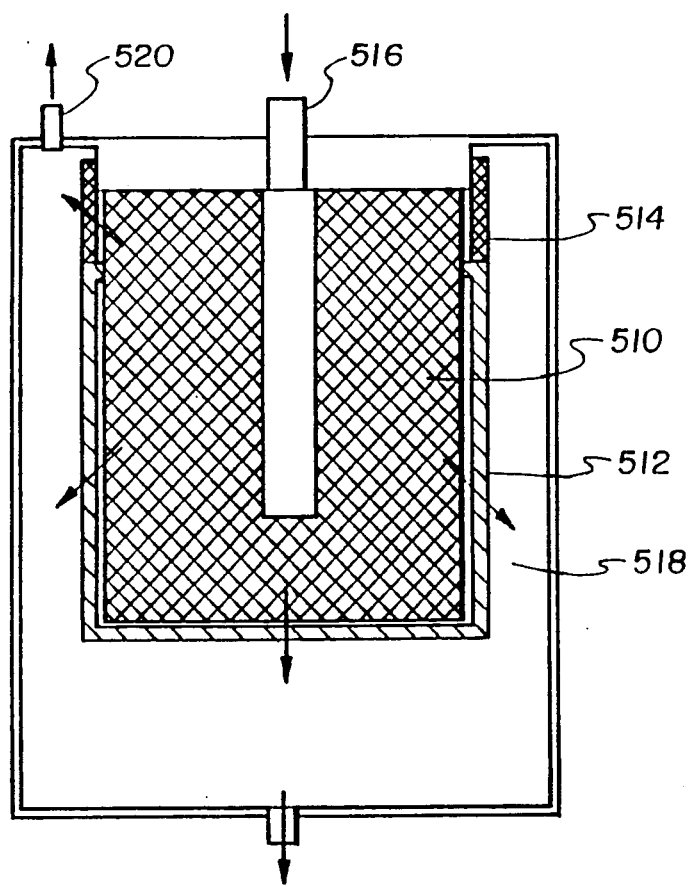
FIG. 9 is a cross-sectional view of an emboli filter for use in the invention.

Diluted blood, or the admixture of blood and washing fluid, then flows into the emboli filter 18 where it is degassified and filtered. The emboli filter may generally be any type of filter which can filter out air from the blood. In a preferred embodiment, as shown in FIG. 9, the emboli filter includes a polyurethane sponge 510 coated with an antifoam silicone compound which assists in the degassification of the aspirated blood. The lower portion of the sponge is covered with a porous filter fabric 512 having a pore size of about 40 microns. The fabric 512 is hydrophilic and allows only blood to permeate therethrough. Polyester is an exemplar fabric for this use. When polyester is wet, it will not allow permeation of air therethrough unless high transmembrane pressure is applied. The upper portion of the sponge 510 is covered with a hydrophobic fabric 514 which does not allow blood to permeate therethrough, but correspondingly allows air to permeate therethrough. Nylon is an exemplar fabric for this purpose. As the blood/washing fluid admixture enters the emboli filter through the inlet port 516, the blood filters through the sponge 510. Air becomes separated from the blood and rises to the top portion of the filter. Blood is filtered through the bottom portion of the filter, and impurities of a larger size (typically greater than 40 microns) are filtered out. The blood collects in the reservoir 518 associated with the emboli filter. A vacuum connector means 520 is provided to which is attached a vacuum source (not shown). Negative vacuum pressure from the vacuum source vents off air separated out by the polyurethane sponge 10 and also applies negative pressure to the blood collected in the reservoir 518 to remove air therefrom.

Referring again to FIG. 1, the blood level in the reservoir 22 is detected by ultrasonic detectors 60 and 64. The ultrasonic detector 64 at the upper portion of the reservoir detects a high level of blood in the reservoir, and the detector 60 in the lower portion of the reservoir detects a low blood level.

The invention provides a continuous on-line method of removing impurities from the blood which are below a specified molecular size. Purified blood which has a specified cellular volume fraction (i.e., hematocrit) value is reinfused. A specified cellular volume fraction may be achieved by recirculating the filtered blood exiting from the outlet port 24. The blood is circulated by means of a roller pump 36 which urges the blood through a membrane filter 38, a flow constrictor 40, a conductivity (i.e., hematocrit) monitor 42, and a recirculation valve 44. The cellular volume fraction of the recirculating blood may be continuously measured using an on-line conductivity monitor 42. Recirculation through the system may be accomplished by any pumping means, including a conventional roller pump 36.

Cellular volume fraction (i.e., erythrocyte count) is measured continuously by the monitor means 42. In a preferred embodiment, the monitor means is a conductivity monitor which constantly measures the conductivity of blood at a specified frequency using two stainless steel electrodes (not shown) at the outlet of the membrane filter 38. Such conductivity monitors 42 are available on the market (e.g., from Sedatelec, Chemin des Muriers, Irigny, France). These electrodes supply a current of ten microamperes to the blood at a frequency of five thousand Hertz. Measured conductivity of blood is known to be proportional to its noncellular volume fraction. Therefore, it noncellular volume is high, more recirculation is needed to remove fluids until a desired amount of cellular blood components remain.

The membrane filter 38 may be any conventional membrane-type separator with a pore size ranging from 40,000 daltons to 400,000 daltons molecular weight cut off. Such filters are known in the art as ultrafilters. It may be preferable to use a membrane with a pore size not exceeding 100,000 daltons. However, if larger size impurities are to be removed, a filter having a pore size of 400,000 daltons, or a plasma filter having a pore size of up to 0.4 micron (a few million dalton molecular weight cut off) can be used. Which membrane filter is used will depend on the types of molecules or blood components the surgeon wants to maintain in the blood for reinfusion. As blood passes through the membrane filter 38, fluid and other components having a size smaller than that of the membrane pores will be removed as filtrate through the filtrate port 46. The filtrate may be collected in a filtrate receptacle 48.

As the fluid is removed from the recirculating blood by the membrane filter 38, the cellular volume fraction (i.e., hematocrit) will increase. When the hematocrit of recirculating blood reaches the specified value, as measured by the conductivity monitor 42, the recirculation valve 44 closes to stop the recirculation procedure. The recirculation valve 44 may be a three way shunt valve which intermittently allows blood to flow through the recirculation pathway, and intermittently occludes that pathway thereby allowing the blood to enter the reinfusion pathway 50.

Blood entering the reinfusion pathway at 50 flows through a venous filter 52, a venous valve 54 and a reinfusion line 56. The venous filter 52 removes any blood clots from the blood prior to its reinfusion. The blood level in the venous filter 52 may be detected by an ultrasonic detector 58. The venous valve 54 normally remains closed (i.e., during recirculation). It opens only when three conditions are met simultaneously. These conditions are: (i) No air bubble must be present in the blood to be infused, as detected by an ultrasonic bubble detector 58; (ii) the level of blood in the reservoir 22 must be above the lower point of the reservoir as monitored by the ultrasonic blood level detector 60; and (iii) the cellular volume fraction of recirculating blood must be equal to or greater than a specified value as monitored by the conductivity monitor 42.

The apparatus as described above provides the patient with his/her own blood which is free of air emboli and which is at a specified cellular volume fraction. The specified cellular volume is to be determined by the attending physician(s) in accordance with the patient's needs.

Figure 2:
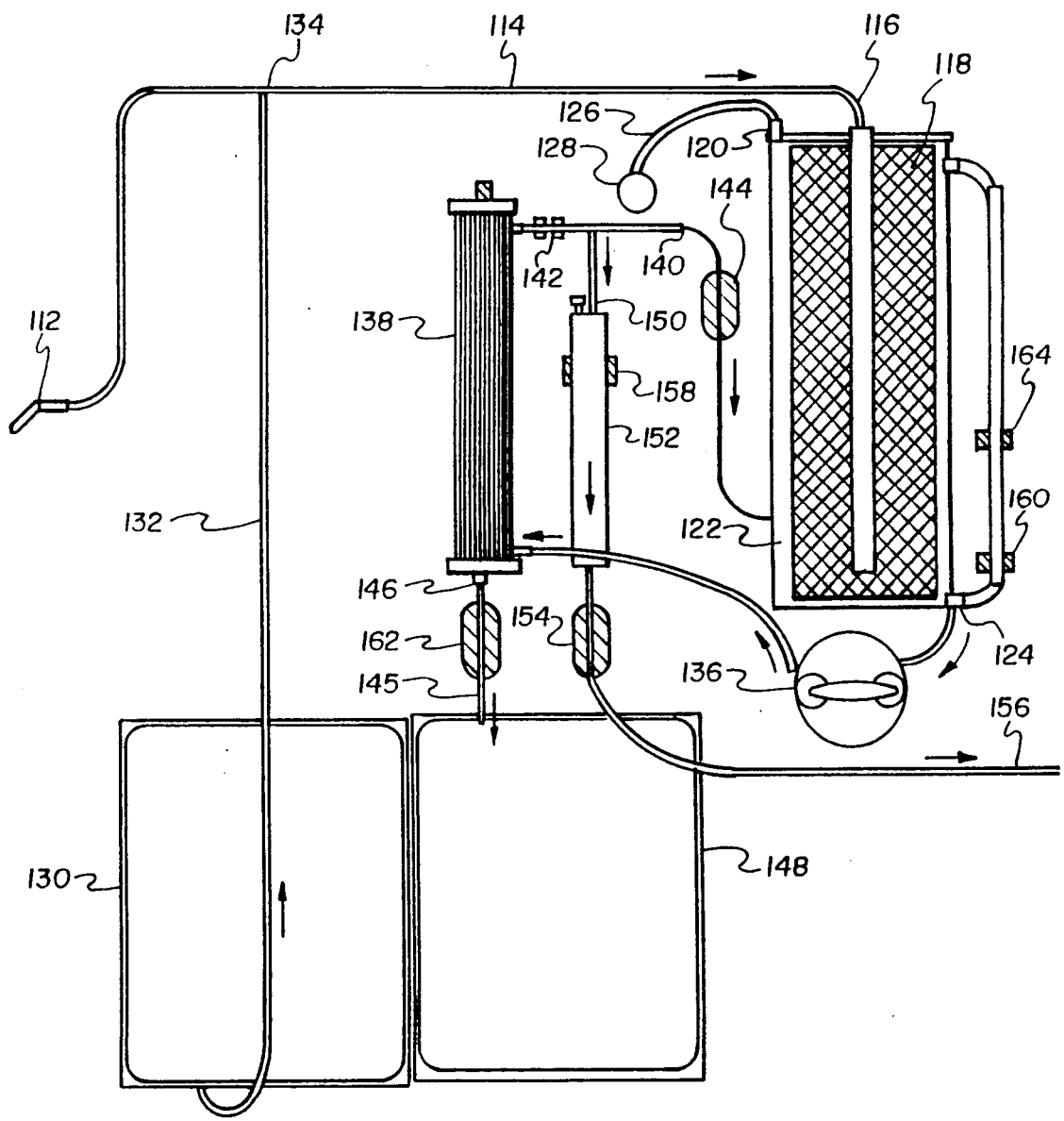
FIG. 2 is a front view of the embodiment shown in FIG. 1.

The embodiment described in FIGS. 1 and 2 provides a simple method of membrane filtration without using any filtrate pump (i.e., a suction pump in the filtrate port 46) or transmembrane pressure difference control. Rather, filtration is accomplished by providing flow constriction means 40 at the outlet of the membrane filter 38. Constriction of the outlet through which blood exits the membrane filter acts to increase transmembrane pressure difference in the membrane filter. Increased transmembrane pressure enhances filtration. Filtrate port 46 is connected to a collapsible filtrate receptacle 48 which collects filtrate (waste) from the membrane filter. A suction pump in connection with the filtrate port 46 may be used, but one need not be used if the objective is to keep the system as simple as possible. Thus, where a filtrate pump is not used, pressure in the filtrate port is constant and is about equal to atmospheric pressure.

It is well known in the art that membrane filtration rate is dependent on the extent of dilution of the blood (i.e., viscosity, hematocrit, plasma protein concentration). Filtration rate increases with increase in dilution of blood for the same transmembrane pressure difference and shear rate (i.e., blood flow rate). Thus, more fluid will be removed from the blood by membrane filtration when the blood is more diluted. It is also known in the present art that filtration rate can also be increased by increasing shear rate and transmembrane pressure difference.

The embodiment shown in FIGS. 1 and 2 provides a method of increasing transmembrane pressure difference and shear rate by increasing the speed of the recirculation pump in proportion to the amount of fluid to be removed from the blood. The amount of fluid to be removed may be determined from the conductivity monitor 42 located in proximity to the outlet of the membrane filter 38 in the recirculation pathway. If the measured value of cellular volume fraction is below a specified limit (e.g., 35%), then a signal is sent to the speed-control of the recirculation pump 36 to increase its speed to a higher value. In other words, the lower the measured cellular volume fraction, the higher will be the pump speed, transmembrane pressure difference, shear rate, and filtration rate.

Alternatively, filtration may be increased as determined by the level of blood in the reservoir 22. Therefore, when the level of blood rises above the level of the blood level detector 64, the speed of the recirculation pump 36 increases. When the level of blood in the reservoir 22 falls below the blood level detector 64, then the speed of the recirculation pump 36 decreases. As a result, the amount of fluid removed from the blood may also be manipulated by the amount of blood in the reservoir for processing.

It should be noted that prior to the operation of this embodiment of the apparatus, washing fluid containing heparin may be circulated through the apparatus to eliminate all the air bubbles from the system. Thus, at the beginning of the flushing procedure, the cellular volume fraction of fluid circulating through the membrane filter may be almost zero. In such a case, rapid filtration may be falsely triggered by the control unit. As a result the level of fluid in the filter reservoir 22 may drop below the set value as determined by blood detector 60 causing air to be sucked into the membrane filter 38. In order to eliminate air being sucked into the membrane filter 38, the filtrate port 46 may be closed by a filtrate valve 62 which closes only when the fluid level in the reservoir 22 falls below the level of the blood level detector 60. The filtrate valve 62 may also be closed when the cellular volume fraction measured by the conductivity monitor 42 becomes equal to or greater than the specified value.

The embodiment described in FIGS. 1 and 2 is directed to function on a real time basis. That is, purified blood will be returned to the patient within a few minutes of aspirating it from the wound site 10.

The apparatus of this embodiment can be more fully understood with reference to FIG. 2, which is generally a front view of the apparatus described in FIG. 1. The components of FIG. 2 have been described in FIG. 1. The suction means 112 is connected to blood inlet port 116 of the emboli filter 118 by suction tubing 114. The vacuum connector means 120 of the emboli filter casing 119 is connected to a controlled vacuum source 128 by a vent line 126 so that controlled negative pressure can be applied to aspirate blood from the wound site into the emboli filter 118. Washing fluid is brought into the suction tubing 114 by increased negative vacuum pressure, as previously described. The washing fluid bag 130 is located about two feet below the emboli filter 118 and, washing fluid flows through the washing fluid line 132 which is connected to the suction tubing 114 by a Y-connector 134.

Aspirated blood mixed with washing fluid enters the emboli filter 118 via the blood inlet port 116. Filtered blood, free of air and particles larger than 40 microns, is collected in the filter reservoir 122. This blood is drawn from the reservoir outlet 124 of the reservoir 122 by the recirculation pump 136. The blood is then circulated through the membrane filter 138, a flow constrictor 140, a conductivity monitor 142, and a recirculation valve 144, and it then returns back to the reservoir 122 for recirculation by the recirculation pump 136. Filtrate leaving the filtrate port 146 is collected in the filtrate receptacle 148.

Recirculation of blood through the membrane filter 138 is intended to continue until the fluid removed from the blood by filtration becomes at least equal to the amount of fluid that was infused into the blood. This may be done by continuously monitoring the conductivity of the recirculating blood using a conductivity monitor 142 located in proximity to the outlet of the membrane filter 138. When the cellular volume fraction becomes equal to or greater than a specified value, recirculation stops by the closing of the recirculation valve 144, and blood is forced to exit the recirculation pathway at 150.

The processed blood leaves the recirculation pathway at 150 and flows into the venous filter 152 where blood clots, if any, are filtered out. Filtered blood leaves the venous filter 152, passing through the venous valve 154 and proceeds to the venous reinfusion line 156. An ultrasonic detector 158 may be provided to detect any air bubbles present in the blood flowing through the venous filter. An additional ultrasonic bubble detector which serves as a blood level detector 160 is provided in order to detect air bubbles in the blood contained in the reservoir 122. Similarly, a blood level detector 164 measures a high level of blood in the reservoir 122.

To ensure safety to the patient, processed autologous blood may not be reinfused until the following three conditions are met: (i) The cellular volume fraction of blood, as measured by the conductivity monitor 142, is at least equal to a set value; (ii) the blood level in the filter reservoir 122 remains above a set value as determined by the blood level detector 160, and (iii) the venous blood in the venous filter 152 does not contain any air bubbles as determined by the ultrasonic detector 158. Only when these three conditions are met does the venous valve 154 remain open to allow reinfusion of blood to the patient. Concurrently, the recirculation valve 144 remains closed. However, whenever one of the aforementioned three conditions is not met, the venous valve remains closed and the recirculation valve remains open to allow continued filtration.

The filtration rate through the membrane filter 138 may be controlled by increasing the recirculation pump 136 speed in proportion to the amount of fluid to be removed. The amount of blood which needs to be processed is determined by the blood level detector 164; that is, when the level of blood is above the blood level detector 164, a signal is sent to the recirculation pump 136 to increase in speed. As noted above, increased filtration increases the amount of fluid removed from the blood. Further, that excess fluid needs to be removed can also be determined by the cellular volume content monitored by the conductivity monitor 142. When the cellular volume fraction decreases, more fluid needs to be removed from the blood, and the recirculation pump is signalled to increase speed.

Figure 3:
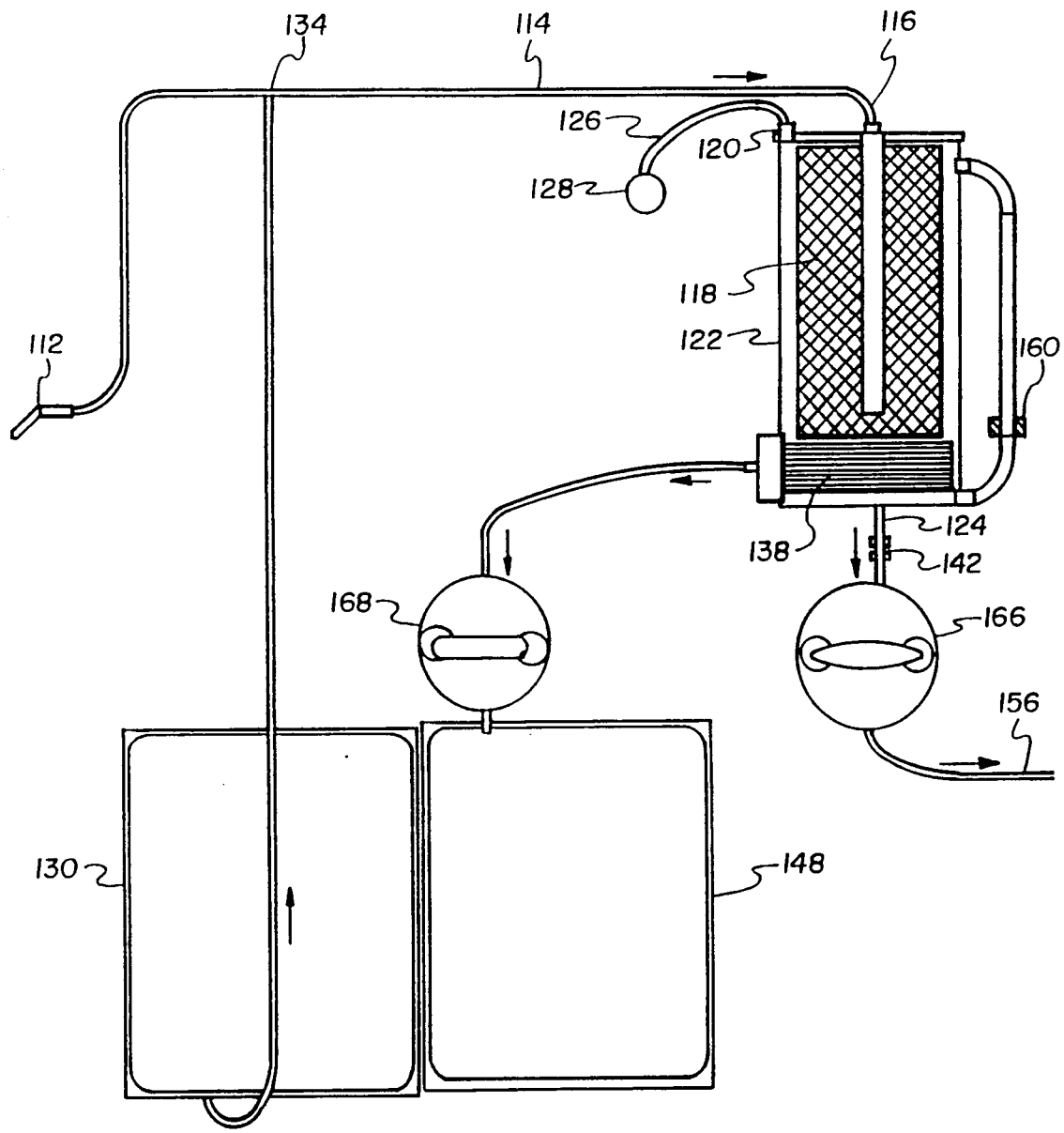
FIG. 3 is a schematic diagram illustrating an alternative embodiment of an intraoperative autotransfusion system using an integrated filter.

FIG. 3 illustrates an alternative embodiment of the system. As with the previous embodiments, suction means 112 is provided for aspirating blood from the wound site; washing fluid is retained in a collapsible bag 130; the washing fluid is infused by increasing negative pressure into the suction tubing 114; and admixed blood and washing fluid enter the emboli filter 118 at the inlet port 116. A vacuum source 128 is connected to the emboli filter casing 119 by a vent line 126 attached to the vacuum connector means 120 which supplies the negative pressure for suction.

In this embodiment, the membrane filter 138 is integrated with the emboli filter 118. The membrane filter 138, in this illustrated embodiment, is positioned below the emboli filter. Filtration across the membrane filter is achieved by a filtration pump (roller pump) 168 which provides negative pressure for filtration. The filtration pump 168 may be operated at a constant flow rate of approximately 200 milliliters per minute (ml/min.). However, when the blood level in the reservoir 122 falls below a set level, as detected by the blood level detector 160, the filtrate pump 168 will stop.

An infusion pump 166 infuses blood from the reservoir 122 to the patient via the venous line 156. The infusion pump 166 will infuse blood to the patient only when two conditions are met: (i) The cellular volume fraction of blood measured by the conductivity monitor 142 is above a set value, and (ii) the level of blood in the reservoir 122 is above the level detected by the blood level detector 160.

It will be appreciated that in the embodiment described in FIG. 3, damage to blood is minimized, and the system is significantly simplified, by eliminating blood recirculation between the membrane filter 166 and the reservoir 122. This is made possible by the integration of the emboli filter 118 and the membrane filter 138. The integrated filter may be denominated as an "integrated cascade filter." This integrated filter may be made by potting a bundle of hollow fibers or tubules together and positioning them at the bottom of an emboli filter in such a way that both the emboli filter and the membrane filter are enclosed by a single reservoir. "Potting", as used herein, is a procedure for affixing together a bundle of hollow tubules using an agent such as glue, resin, polymers and the like. Alternatively, the bundle of hollow fibers which comprise the membrane filter portion of the integrated filter may encircle the emboli filter to strain and filter out excess fluid as the blood exits the wall of the emboli filter. The membrane filter may also be a flat membrane shaped like a hollow cylindrical drum positioned proximate to the emboli filter, and may be mechanically rotated (e.g., by motor means) to increase circulation of the blood. Membrane filters of this type are manufactured by Baxter Labs. of Deerfield, Ill.

The embodiments illustrated in FIGS. 4, 5, 10, and 12 are embodiments directed to disposable units which are easily manipulated, positioned, operated, and disposed of after use. It is the objective of these embodiments to present a simplified apparatus for use during intraoperative or post-operative procedures.

As in the previously described embodiments, the apparatus generally includes an emboli filter casing 119 to which is attached a vacuum source 128 via a vent line 126 of tubing which connects to the emboli filter casing at the vacuum connector means 120. A source of vacuum is readily available in most surgical settings. The vacuum source applies a negative pressure to the emboli filter 118, which is positioned within the emboli filter casing 119. The negative pressure of the vacuum source should be regulated from about −125 to about −200 mm Hg. Insufficient vacuum will prohibit proper aspiration of blood, and washing fluid, into the system; however, excessive negative pressure will ultimately damage the blood cellular components, and may cause aspiration of blood from the reservoir 122 into the vacuum source 128.

Figure 4:
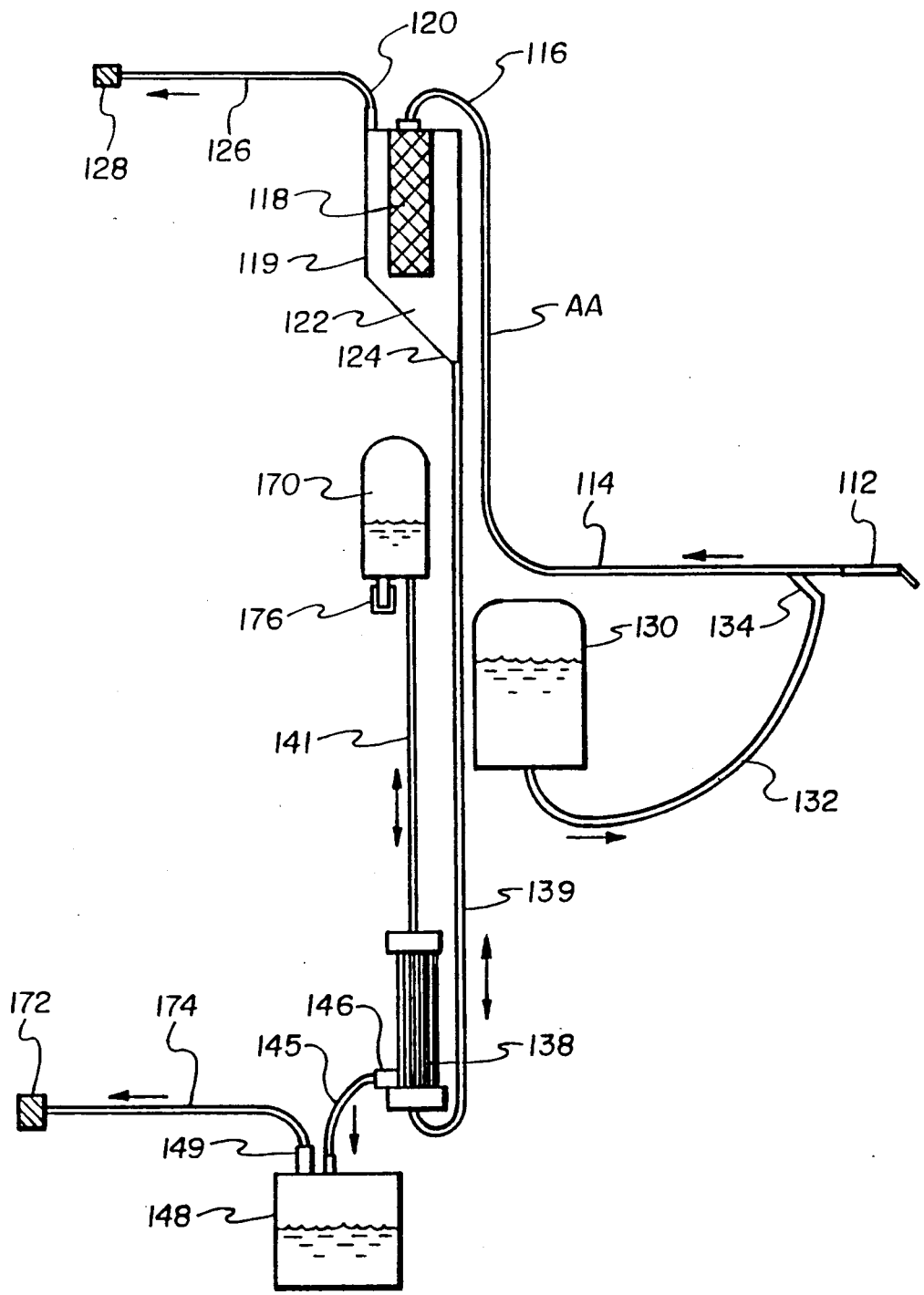
FIG. 4 is a schematic diagram of a machineless intraoperative autotransfusion system.

The embodiment of FIG. 4 includes suction means 112 for aspirating blood from the wound site. The suction means 112 is generally comprised of a handle for gripping by the surgeon or medical personnel, and a tip for placement into the blood source formed at the wound site. The handle is connected to a length of suction tubing 114 which connects to the blood inlet port 116 of the emboli filter 118. The suction tubing 114 may be composed of any flexible material typically used in surgical equipment, including rubber, plastic, and the like.

A flexible plastic bag 130 containing washing fluid, and anticoagulant if desired, is connected to the suction tubing 114 via washing fluid line 132 by means of a Y-connector 134. The Y-connector 134 may be positioned along the suction tubing 114 anywhere from approximately adjacent the suction means 112 to approximately adjacent the blood inlet port 116 of the emboli filter. The washing fluid bag 130 must be maintained approximately two feet below the level of the suction means 112. So positioned, the amount of fluid being drawn into the suction tubing 114 as a result of the negative pressure applied by the vacuum source 128 will approximately equal the amount of blood being aspirated into the suction tubing 114 from the wound site. It will be recognized that adjusting the height of the washing fluid bag 130 above or below the above-specified height relative to the suction means 112 will result in more or less washing fluid being drawn into the suction tubing 114, respectively.

Further, the equal ratio of aspirated washing fluid to aspirated blood may be maintained with an increase or decrease in the suggested height of the washing fluid bag 130, relative to the suction means 112, coupled with a corresponding decrease or increase in size of the tubing of the washing fluid line 132.

Aspirated blood and washing fluid mix together at the intersection of washing fluid line 132 and the suction tubing 114 at the Y-connector 134. The blood/washing fluid admixture is drawn through the suction tubing 114 by means of negative pressure, and enters into the emboli filter 118. The emboli filter 118 is enclosed within the emboli filter casing 119 which is comprised of a hard or otherwise suitably non-collapsible material. The space between the emboli filter 118 and the emboli filter casing 119 defines the reservoir 122. The emboli filter 118 may be any standard filter which has the capability of removing particulate matter and air bubbles. The emboli filter illustrated in FIG. 9, as described above, is preferred. As blood enters the emboli filter 118, large particulates are filtered out and air bubbles are directed to the upper portion of the filter as described above. The negative pressure of the vacuum source draws the air bubbles away from the filter. The filtered blood drains through the filter and collects in the reservoir 122. If any air bubbles remain in the filtered blood retained in the reservoir 122, they are further subjected to negative pressure from the vacuum source, and are drawn into the vent line 126 thereby.

It is contemplated that the components of the embodiment shown in FIG. 4 may preferably be attached to a standard I.V. pole, or similar device. The emboli filter 118 should be placed on the I.V. pole approximately six feet above the ground. At that level, the emboli filter is approximately two to three feet above the level of the patient on the operating table. The emboli filter may be positioned from about two feet to about five feet above the relative height of the patient. Aspiration of blood from the would site is maximized at that range of heights. That is, an average negative pressure of −120 mm Hg can raise a column of blood approximately five feet; therefore, the relative height of the emboli filter above the patient should not exceed five feet. Flow resistance in the conduit is also affected by the diameter of the conduit. Therefore, the suction tubing 114 should range in diameter from about 5 mm to about 20 mm, with a preferred diameter of 10 mm. Filtered blood collected in the reservoir 122 flows downwardly to the membrane filter 138 via the conduit 139, which is interconnected between the emboli filter casing 119 at the outlet port 124 and the membrane filter 138. The emboli filter may be positioned from about six feet to about nine feet above the membrane filter, and a preferred relative height is about seven feet above the membrane filter. At that height, blood is able to flow by gravity through the conduit 139 to the membrane filter 138, and there is sufficient negative pressure exerted on the conduit 139 to allow back-flow of blood for the filtration process, as described below. To maximize flow through the conduit 139, the diameter of the tubing should be from about 4 mm to about 8 mm with a preferred diameter of 6 mm. The length of conduit 139 should be from about six feet to about nine feet.

The membrane filter 138 is located approximately at ground level to about one foot above ground level on the I.V. pole. Hydrostatic forces and gravity force the blood to pass through the membrane filter 138 and into the blood collection bag 170 via the second conduit 141, interconnected between the membrane filter 138 and the blood collection bag 170. The blood collection bag is made of flexible plastic, or similar material, which has been evacuated of air prior to use. The blood collection bag 170 is preferably positioned approximately five feet above the height of the membrane filter. The diameter of second conduit 141 may range from about 4 mm to about 10 mm, with a preferred diameter of 6 mm. The blood collection bag 170 has a port means 176 from which the blood may be infused back into the patient when the bag becomes full.

As the blood passes through the membrane filter 138, it passes through the small porous tubules of the membrane filter which separates out excess fluid and very small particles. The filtrate which is separated from the blood exits the membrane filter 138 at filtrate port 146, and enters into the filtrate receptacle 148 via a filtration line 145 connecting the filtrate receptacle 148 to the filtrate port 146. A vacuum source 172 may optionally be connected to the filtrate receptacle 148 by means of tubing 174 connected to the vacuum port 149 of the filtrate receptacle 148. The filtrate receptacle is correspondingly comprised of a rigid material, such as hard plastic or the like. The negative pressure applied to the filtrate receptacle 148 may range from about −60 mm Hg to about −200 mm Hg.

It may be appreciated that when there is bleeding at the wound site, the tip of the suction means 112 placed into the pool of blood causes negative pressure to increase, thereby causing blood and washing fluid to be sucked into the suction tubing 114 and into the emboli filter 118. When bleeding slows or stops, the lack of fluid being aspirated into the suction tubing 114 causes the negative pressure to drop to approximately −80 mm Hg, and no fluid is aspirated into the emboli filter 118. During this period of reduced negative pressure, blood and washing fluid which has been aspirated previously into the emboli filter, filters therethrough and collects in the reservoir 122. By gravity, it then passes through conduit 139 into the membrane filter 138. Hydrostatic pressure further forces the blood through the membrane filter 138 into the blood collection bag 170. If a vacuum source 172 has been connected to the filtration receptacle 148, the negative pressure thus applied acts to draw filtrate from the membrane filter 138, and may collaterally act to urge blood from the reservoir 122 to the blood collection bag 170. The amount of filtration which takes place at this time is dependent upon the transmembrane pressure difference (TMP). The TMP is dependent upon the height of the reservoir 122, on the height of the blood collection bag 170, and the level of negative pressure.

When blood is present at the wound site for aspiration, and is aspirated into the system via the suction means 112, negative pressure increases. Concurrently acting to aspirate blood and washing fluid into the emboli filter, the negative pressure also acts to draw the blood from the blood collection bag 170 back through the membrane filter 138, and into the reservoir 122. When bleeding subsides, and there is a concomitant drop in negative pressure, the blood passes back down through the membrane filter 138 and into the blood collection bag 170. With each pass through the membrane filter, more fluid and small particles are removed as filtrate.

When a sufficient amount of blood has collected in the blood collection bag 170, the blood collection bag 170 can be removed from the second conduit 141, and can be replaced by another flexible bag from which all the air has been evacuated. The blood collected in the removed bag may then be infused back into the patient from outlet port 176. Alternatively, the blood collection bag 170 may remain in place for infusion to the patient. In that situation, the negative pressure supplied to the system by the vacuum source 128 must remain low. Preferably, a clamp should be placed on the second conduit 141 to prevent blood from entering or exiting the blood collection bag 170.

Before reinfusing, the amount of fluid collected in the filtrate receptacle 148 should be compared with the amount of washing fluid which was infused into the aspirated blood. The amount of fluid in the filtrate receptacle 148 should be roughly equal to the amount of fluid infused into the system. If it appears that less fluid has been recovered than was infused into the system, the blood may be continuously circulated through the membrane filter 138 by periodically applying pressure to the suction tubing 114 at point AA, as shown in FIG. 4. By applying pressure, such as by squeezing the suction tubing 114 between the thumb and forefinger, negative pressure increases in the emboli filter 118 and blood from the blood collection bag 170 is urged through the membrane filter 138 toward the reservoir 122. When the pressure is released, the negative pressure decreases again, and gravity causes the blood to circulate through the membrane filter 138 toward the blood collection bag 170. By intermittent application of pressure, the blood may be effectively recirculated through the membrane filter until a sufficient amount of fluid has been removed. Pressure may also be applied to the suction tubing 114 by use of a mechanical clamp.

Figure 5:
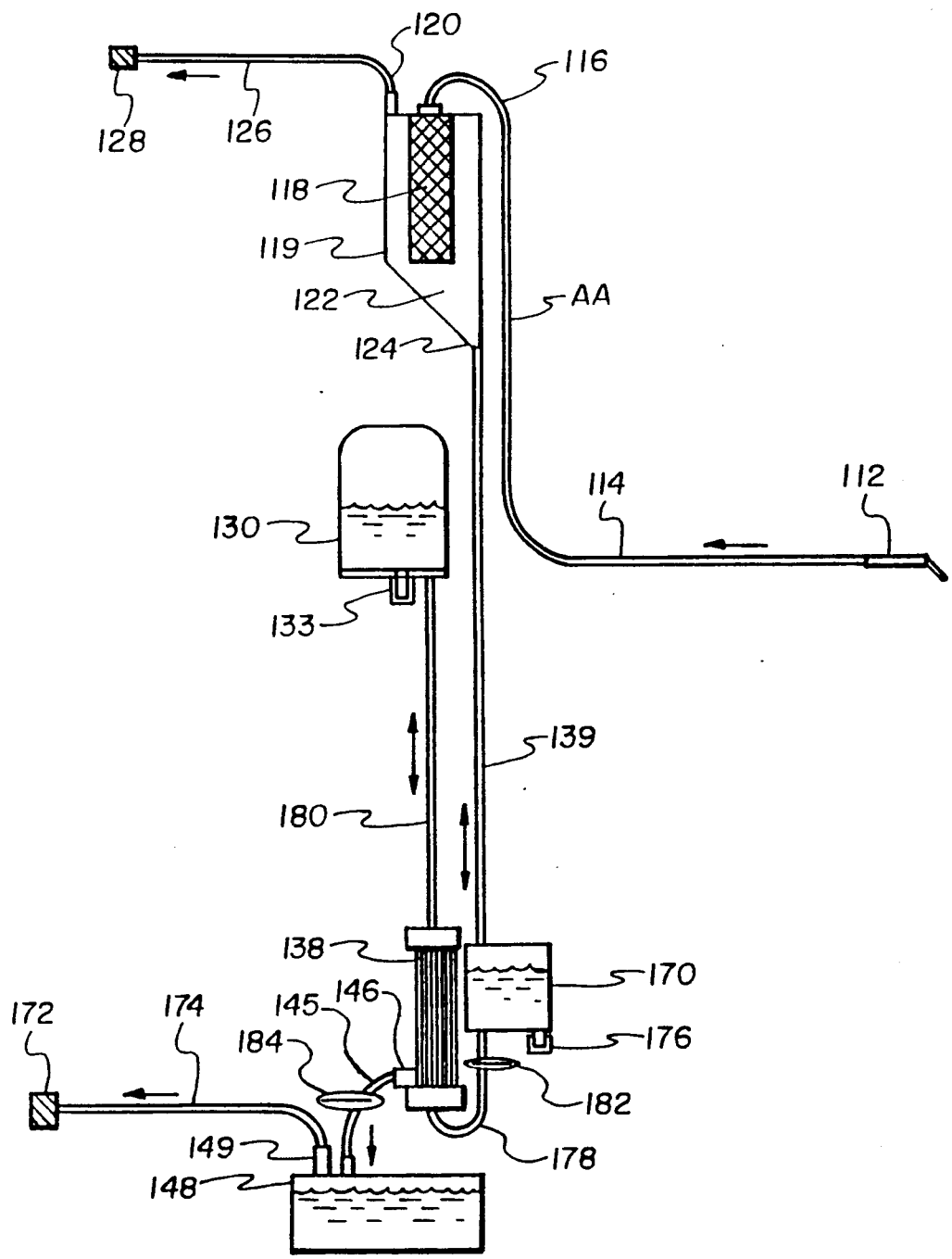
FIG. 5 is a schematic diagram of an alternative embodiment of a machines interoperative autotransfusion system.

FIG. 5 illustrates an alternative embodiment to the simple configuration shown in FIG. 4. This embodiment presents a different method of introducing washing fluid into the aspirated blood for the washing procedure. As with the previously described embodiments, blood is aspirated from the wound site by suction means 112 under negative pressure supplied by a vacuum source 128 connected to the emboli filter casing 119. The aspirated blood is directed to the emboli filter 118 by suction tubing 114, and the blood enters the emboli filter 118 at the blood inlet port 116. Blood is immediately filtered through the emboli filter 118 as described above, and the blood is collected in the reservoir 122. In this embodiment, however, the filtered blood is thereafter directed, by gravity, to a blood collection bag 170, which is positioned approximately one to three feet above the ground on the I.V. pole (not shown). Blood flows from the reservoir 122 to the blood collection bag 170 via a conduit 139 which is interconnected between the outlet port 124 of the emboli filter casing 119 and the blood collection bag 170. The relative positions of the washing fluid bag 130, the emboli filter 118, the membrane filter 138, and the suction means 112 are those described hereinabove with respect to FIG. 4.

A clamp 182 may be placed on the tubing 178, which interconnects the blood collection bag 170 and the membrane filter 138, below the blood collection bag 170 to prevent blood from circulating further through the system. The blood collection bag 170 may contain a precalculated amount of an anticoagulant to prevent clotting of blood accumulated therein. If necessary, the blood may be reinfused to the patient at this point through the reinfusion port 176. The emergency of the situation may require that the blood be reinfused to the patient without further filtration.

Under less exigent conditions, the blood may be filtered further by allowing filtered blood to collect in the blood collection bag 170. When the blood collection bag 170 is partially full, the clamp 182 may be released or removed from the tubing 178 interconnected between the blood collection bag 170 and the membrane filter 138. Removal of the clamp 182 allows washing fluid retained in the washing fluid bag 130, which is positioned above the membrane filter 138, to pass through the membrane filter 138 and into the blood collection bag 170. The washing fluid is generally urged into the blood collection bag through gravitational forces by manipulating the height of the washing fluid bag means 130 relative to the blood collection bag 170. That is, a medical attendant may raise the washing fluid bag 130 above the level of the blood collection bag 170 to urge washing fluid into the blood collection bag 170, followed by lowering the washing fluid bag 130 below the level of the blood collection bag 170 to urge the admixed blood and washing fluid back into the washing fluid bag 130. During this time, the filtrate clamp 184 should remain closed to prevent filtration of the washing fluid.

Recirculation of the blood/washing fluid admixture may be accomplished by sequentially lowering and raising the height of the washing fluid bag 130 in relation to the blood collection bag 170. The admixture of blood and washing fluid is thereby made to circulate between the blood collection bag 170 and the washing fluid bag 130 via the membrane filter 138. During this period of recirculation, the filtrate clamp 184 located on the filtration line 145 is removed, and excess fluids and unwanted components removed by the membrane filter 138 exit via the filtrate port 146 into the filtration line 145 and into the filtrate receptacle 148. Filtration may be enhanced by application of a vacuum pressure by attaching a vacuum source 172 to the filtrate receptacle 148 via a vacuum line 174.

When the amount of fluid in the filtrate receptacle 148 roughly equals the amount of fluid which was originally in the washing fluid bag 130, the filtrate clamp 184 may be replaced on the filtration line 145, and the resulting filtered blood is urged into the blood collection bag 170 by manipulation of the washing fluid bag 130 to an elevated height. The filtered blood is thereby urged, by gravitational forces, into the blood collection bag 170. The clamp 182 below the blood collection bag 170 is secured on tubing 178 and the blood may then be reinfused to the patient from the reinfusion port 176. Alternatively, the blood may be urged into the washing fluid retainer 130, a clamp (not shown) may be connected to the tubing 180 interconnected between the washing fluid bag 130 and the membrane filter 138, below the blood collection bag 170, and the blood may then be infused from port 133.

It may be appreciated that the embodiments shown in FIGS. 4 and 5 are particularly useful in processing blood from a wound site in a batch process when bleeding is intermittent or slow. However, the embodiments of FIGS. 4 and 5 are configured such that blood cannot be continuously processed, or infused back to the patient, when bleeding is constant or heavy because the increased negative pressure during aspiration causes blood collected in the blood collection bag 170 to back up into the reservoir 122. As a result, it is difficult to collect blood continuously in the blood collection bag.

Figure 10:
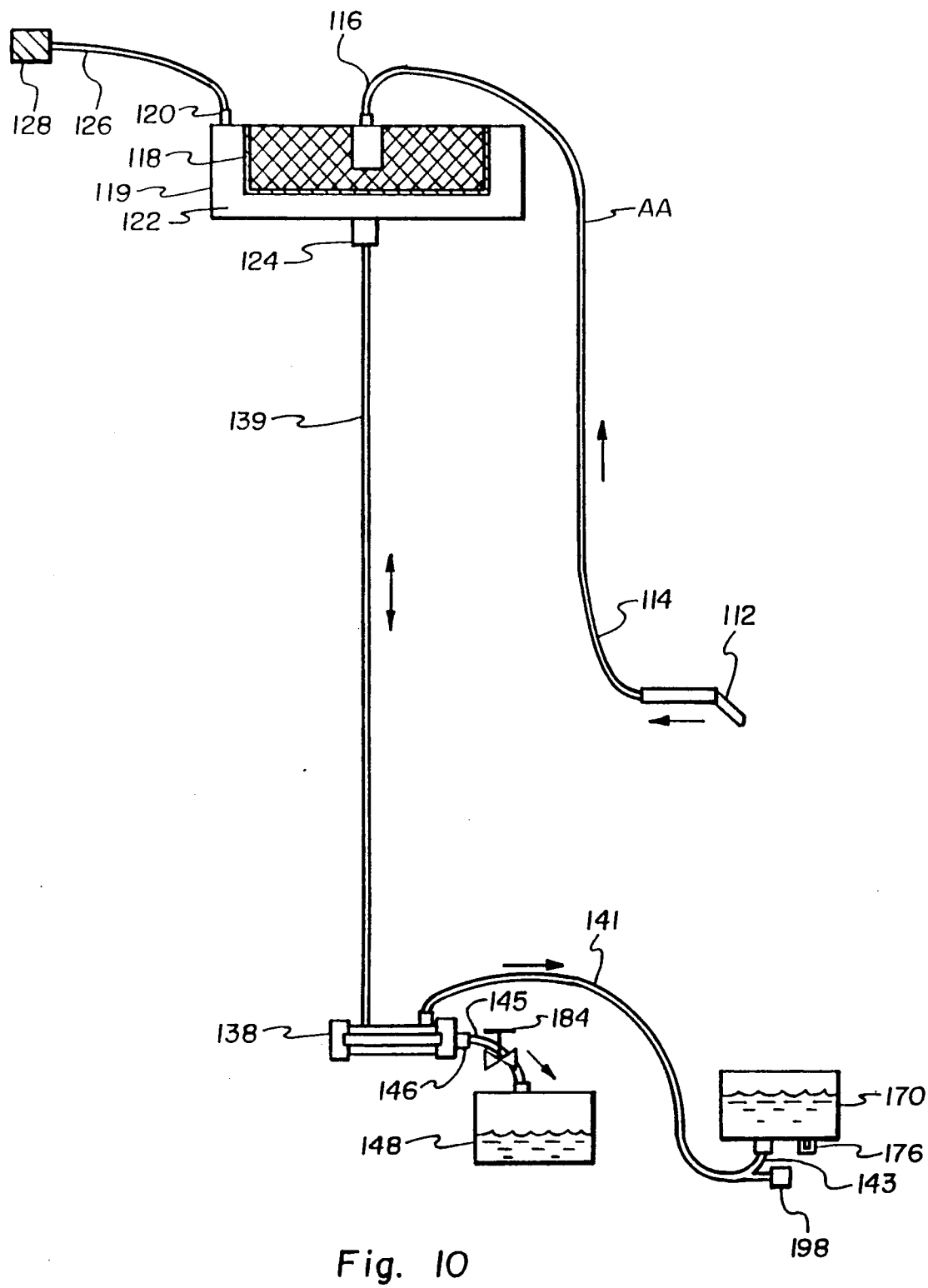
FIG. 10 is a schematic diagram of a simplified embodiment of the invention for use during episodes of less bleeding.
Figure 12:
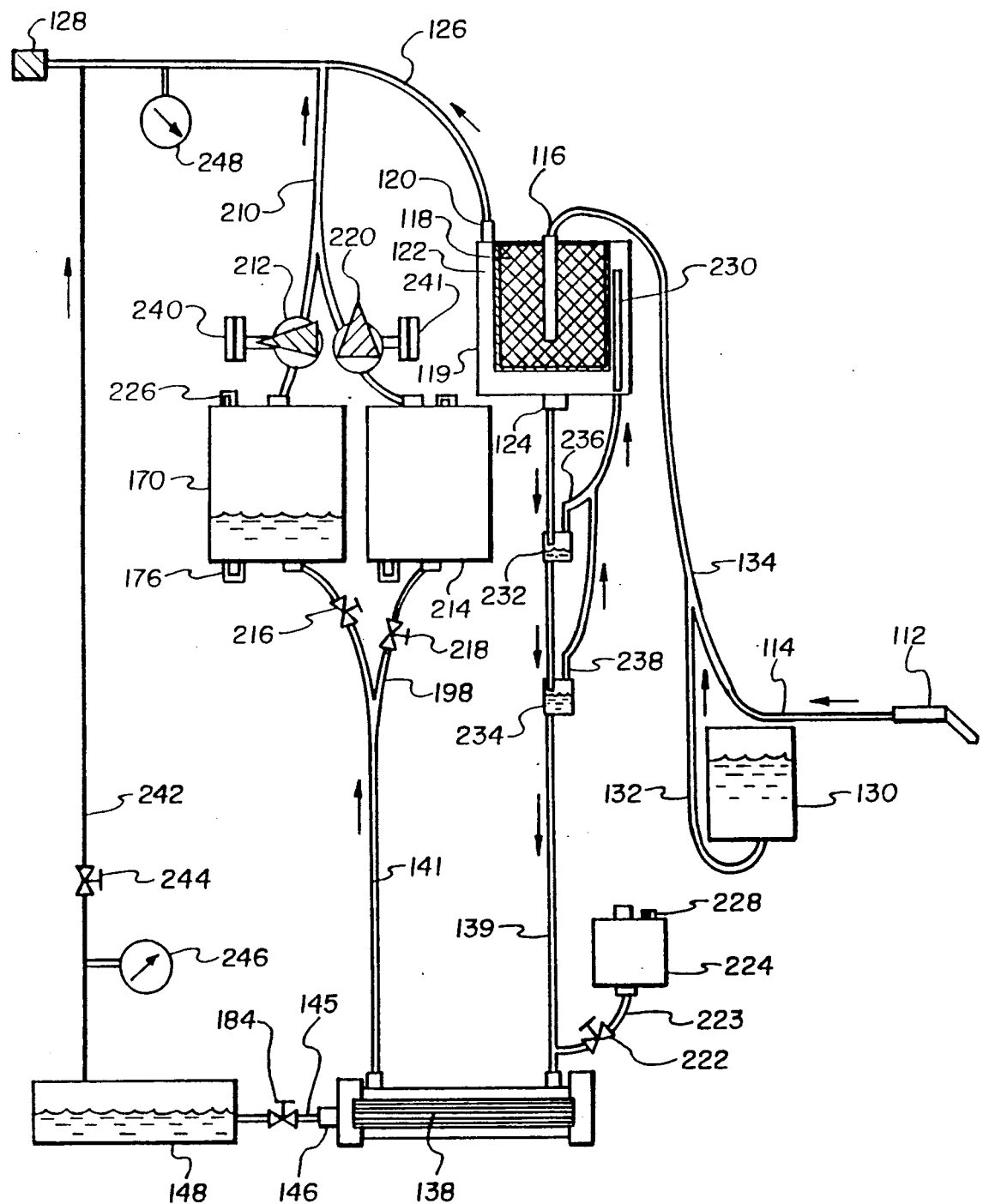
FIG. 12 is a schematic diagram of an alternative embodiment of a simplified version of the invention in which vacuum is applied to the blood collection bag and filtration receptacle.

The embodiments illustrated in FIGS. 10 and 12, therefore, are configured for use during heavy or constant bleeding episodes when blood needs to be infused back into the patient immediately, with or without washing the blood with washing fluid. As shown in FIG. 10, suction means 112 for aspirating blood from the wound site is connected, via suction tubing 114, to the emboli filter 118 at the blood inlet port 116. The emboli filter 118, as with the previously described embodiments, is positioned within an outer emboli filter casing 119 comprised of a rigid material, such as plastic or the like. A vacuum source 128 is connected to the emboli filter casing 119 via a vent line 126 of tubing which connects to the vacuum connector means 120 of the emboli filter casing 119. Negative pressure is thereby supplied to the emboli filter ranging from about $-125$ mm Hg to about $-200$ mm Hg.

The apparatus of FIG. 10, like those of FIGS. 4 and 5 is preferably attached to an I.V. pole or the like. The outlet port 124 of the emboli filter casing 119 should be maintained at least six feet above the ground level. The conduit 139, interconnected between the outlet port 124 and the membrane filter 138, should be at least 5.50 feet in length. The membrane filter 138 and the blood collection bag 170 should be maintained at or near ground level.

In this embodiment, blood from the wound site is aspirated directly into the emboli filter 118 without being admixed first with washing fluid. The aspirated blood enters the emboli filter 118 where large particulates and air bubbles are removed, as described above. Blood drains from the emboli filter 118 and collects into the reservoir 122 formed between the emboli filter casing 119 and the emboli filter 118.

By gravitational force, the blood collecting in reservoir 122 travels down conduit 139, through the membrane filter 138, and into the blood collection bag 170 via the second conduit 141 interconnected between the membrane filter 138 and the blood collection bag 170. It should be noted that the second conduit 141 may be bifurcated so as to enable the attachment of more than one blood collection bag thereto. The blood collection bag 170 is preferably a flexible material, such as plastic or rubber, and may be empty, or may be pre-filled with washing fluid.

If the surgeon predicts that blood infusion to the patient must take place immediately upon aspiration, the blood collection bag 170 will not be pre-filled with washing fluid. Instead, filtered blood descending into the blood collection bag 170 from the reservoir 122 may be infused immediately into the patient by connecting an infusion line to the reinfusion port 176 of the blood collection bag 170.

When time permits, and washing of the blood is desired, the blood collection bag 170 is pre-filled with washing fluid. The blood collection bag may be pre-filled with washing fluid prior to surgery by placing the suction means 112 into a source of washing fluid and aspirating a desired amount of fluid. The washing fluid filters through the emboli filter and descends through the conduit 139 into the blood collection bag 170. During this time, filtrate clamp 184 must be in place on the filtration line 145 to prevent loss of fluid into the filtration receptacle 148. The blood collection bag 170 may also be pre-filled with washing fluid prior to its attachment to the second conduit 141.

As blood is aspirated through the suction means 112, negative pressure (about $-120$ mm Hg) typically forces the washing fluid from the blood collection bag 170 through the membrane filter 138 into the conduit 139. However, negative pressure of $-120$ mm Hg can only lift fluid to a height of about 5.3 feet in a conduit 139 having a diameter of about 6 mm. As aspirated blood enters the emboli filter 118 and filters into the reservoir 122, the blood thereafter descending through the conduit 139 begins to mix with washing fluid therein.

A negative pressure of $-120$ mm Hg can only raise blood 5.04 feet when the diameter of the conduit is about 6 mm. Therefore, the height of the outlet port 124 of the emboli filter casing 119 must be kept at a height proportional to the negative pressure applied by the vacuum source 128. That is, the blood level in conduit 139 achieves a height of 5.04 feet above the ground level, the negative pressure equalizes the gravitational force exerted on the column of blood. Since the length of the conduit is greater than at least six feet, the force of blood descending from the reservoir 122 through the outlet port 124 into the conduit 139 applies additional hydrostatic pressure thereby causing the blood to flow downwardly in the conduit 139. The greater the height of the emboli filter casing 119, the greater will be the blood flow downwardly through the conduit 139. However, the upper limit of the height of the emboli filter 118 is defined by the relative height between the emboli filter 118 and the surgical table. That is, with an applied pressure of $-120$ mm Hg, only 5.04 feet of blood can be raised. Therefore, in order to facilitate the aspiration of blood from the wound site into the emboli filter 118, the surgical table or wound site cannot be more than 5.04 feet below the height of the emboli filter.

Figure 11:
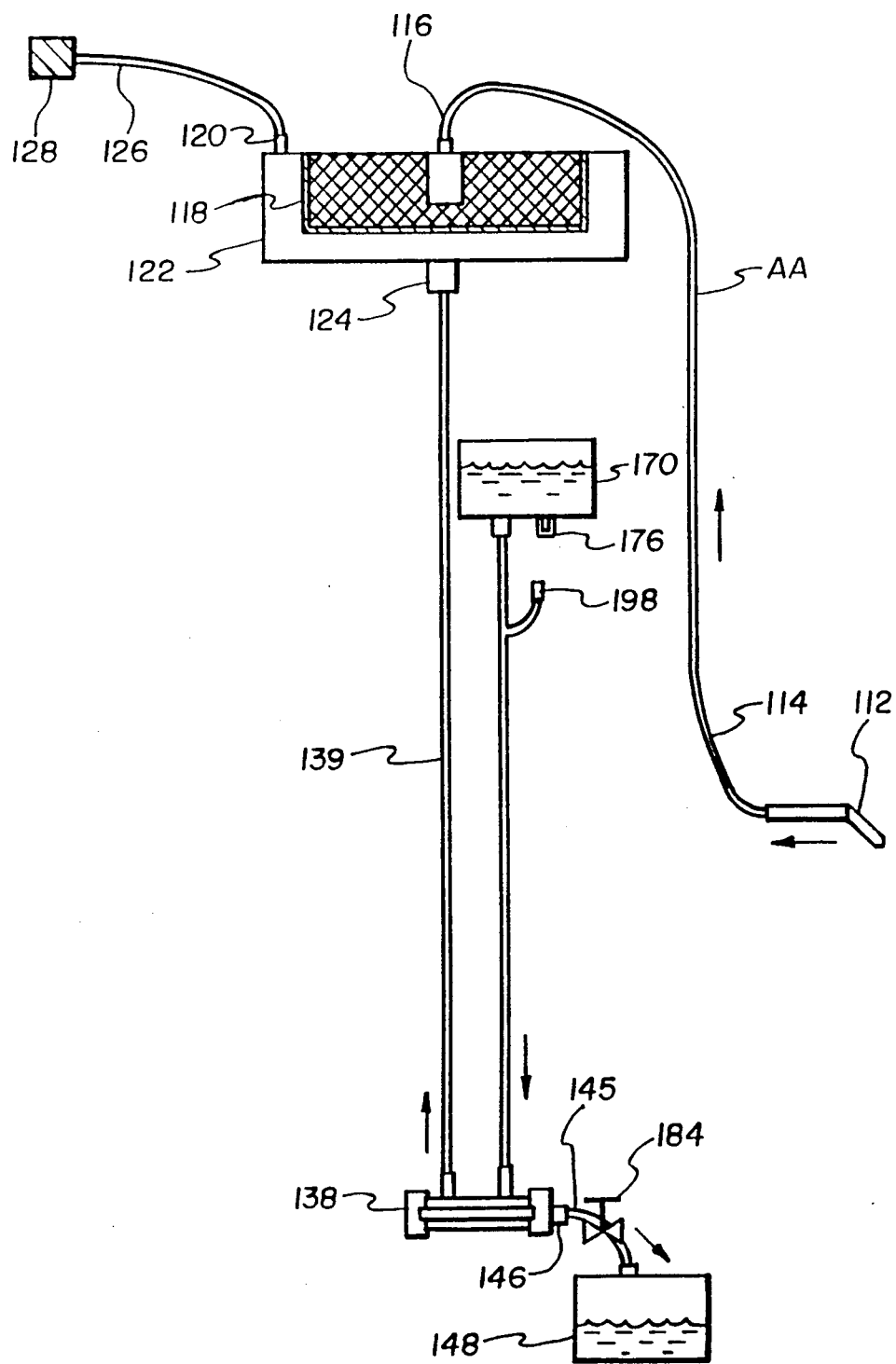
FIG. 11 is a schematic diagram of the embodiment illustrated in FIG. 10 in which the blood collection bag is repositioned.

Mixture of the blood with washing fluid can be enhanced by raising the level of the blood collection bag 170 to a height of approximately six feet above the ground, as illustrated in FIG. 11. Blood and washing fluid will flow back through the membrane filter 138 and partially into the conduit 139. This mixing can take place even during aspiration of blood since the gravitational force in the conduit 139 is still sufficient to force blood downwardly. When the blood and washing fluid have been mixed sufficiently, the filtrate clamp 184 on the filtration line 145 is removed so that filtration may begin. As the blood passes through the membrane filter 138, excess fluids and very small particles are removed. The filtrate flows out from the membrane filter 138 to the filtrate receptacle 148 through the filtration line 145 interconnected therebetween.

When sufficient fluid has been removed from the blood, as determined by comparing the amount of fluid observed in the filtrate receptacle 148 to the amount of washing fluid which was originally placed in the blood collection bag 170, the filtrate clamp 184 is replaced on the filtration line 145. The blood is then collected back into the blood collection bag 170 by lowering the bag to the ground level. Another blood collection bag is attached to the bifurcated line of the second conduit 141 at connection means 198. The blood collection bag 170 is then removed from the second conduit line 141 by applying pressure to the second conduit 141. Blood may then be infused to the patient by attaching an infusion line to the infusion outlet port 176 of the full blood collection bag 170.

FIG. 12 presents an alternative embodiment for collecting purified blood wherein the blood collection bag 170 is connected to a source of negative pressure. The filtrate receptacle 148 is also connected to a source of negative pressure. As a result, the blood collection bag 170 does not need to be raised and lowered manually to admix and filter the blood and washing fluid through the membrane filter 138.

In FIG. 12, blood is aspirated from the wound site via the suction means 112, and blood is carried to the emboli filter 118 by the suction tubing 114. As in previously described embodiments (FIGS. 4 and 5), a washing fluid bag 130, which is maintained at a level approximately two feet below the level of the suction means 112, is connected to the suction tubing 114 by a Y-connector 134. Washing fluid is lifted from the washing fluid bag 132 by negative pressure and is carried through the washing fluid line 132 to the suction tubing 114 at the Y-connector 134. There, washing fluid is admixed with aspirated blood. The admixture of blood and washing fluid is aspirated into the emboli filter 118 where it is filtered and collected in the reservoir 122.

As in the embodiment of FIG. 10, the emboli filter casing 119, and the outlet port 124, should be kept approximately six feet above ground level. the membrane filter 138 should be kept at or about ground level. The filtered blood collecting in the reservoir 122 descends through the conduit 139, into the membrane filter 138, through the second conduit 141, and into the blood collection bag 170.

Occasionally, blood descending through the conduit 139 may contain air bubbles which are not filtered out by the emboli filter 118, or by application of negative pressure upon the emboli filter casing 119. When large air bubbles become trapped in the conduit 139, the average density of the blood and air in the tube decreases, thereby decreasing the flow of blood in the conduit 139. To prevent the entrapment of bubbles, bubble traps 232, 234 are integrated into the conduit 139 to remove the air. Each bubble trap 232, 234 is subjected to the negative pressure from the vacuum source 128 as a result of being in communication with the emboli filter casing 119 through a vent line 236, 238 interconnected between the bubble trap 232, 234 and a vent tube 230 disposed within the emboli filter casing 119. The vent tube 230 is open at its upper end to the upper portion of the reservoir 122, which is most significantly subjected to vacuum pressure. With the open end of the vent tube 230 disposed at the upper portion of the reservoir 122, it is unlikely that blood will enter the vent tube 230 opening.

The bubble traps used in the embodiment may be standard bubble traps, typically used in hemodialysis equipment, which are comprised of an expansion chamber. The expansion chamber of the bubble trap has three openings: an inlet through which blood may enter, an outlet through which blood may exit, and an opening for venting air therethrough. A plurality of bubble chambers may be disposed along the length of the conduit 139 in order to prevent bubble entrapment along its length.

As the admixture of blood and washing fluid passes through the membrane filter 138, excess fluids are removed from the admixture. It is understood that the filtrate clamp 184 on the filtration line 145 is in the open position during this time to allow filtrate draining from the membrane filter 138 to exit through the filtration line 145 into the filtrate receptacle 148. The filtrate receptacle 148 is a non-collapsible container to which vacuum pressure may be applied. As illustrated in FIG. 12, the filtrate receptacle may be attached to the same vacuum source 128 which is connected to the emboli filter casing 119. The vacuum source 128 and filtrate receptacle 148 are interconnected by a vacuum line 242.

Negative vacuum pressure may be applied to the filtrate receptacle 148 in order to enhance filtration through the membrane filter 138. If connected to the same vacuum source 128 as that to which the emboli filter casing 119 is connected, the vacuum pressure applied to the filtrate receptacle 148 is to be regulated by means of a regulator valve 244 to maintain a lower degree of pressure than is provided to the emboli filter casing 119 (i.e., 120 mm Hg). If a plasma filter is being used, the negative pressure applied should be from between about −60 mm Hg to about −120 mm Hg. If an ultrafilter is being used, the negative pressure applied should be from between about −90 mm Hg to about −200 mm Hg. Pressure applied to the filtrate receptacle 148 may be determined by a pressure indicator 246 on the vacuum line 242. It may also be noted that when negative pressure increases during aspiration of bleeding, the negative pressure to the filtrate receptacle 148 correspondingly increases as a result of being interconnected to the same vacuum source 128. When negative pressure decreases during little or no aspiration of blood, the vacuum pressure in the filtrate receptacle 148 correspondingly decreases. Therefore, filtration increases when blood is being actively aspirated, and filtration decreases when blood is not being aspirated.

In this embodiment, more than one blood collection bag is provided so that infusion can take place from one bag while the other bag is filling with blood. Further in this embodiment, both blood collection bags, which are non-collapsible, are connected to a vacuum source, or to the same vacuum source 128 to which the emboli filter casing 119 is attached. The vacuum line 210 to the collection bags 170 and 214 is connected to the vent line 126 which is connected to the emboli filter casing 119. The vacuum line 210 to the collection bags 170, 214 is bifurcated, by means of a Y-connector or similar device, into separate vacuum lines to each blood collection bag.

The separate vacuum line to each blood collection bag is fitted with a two-way valve 212, 220 which can either supply vacuum pressure to the individual blood collection bag, or can produce atmospheric pressure by closing the valve to the negative pressure. Each valve 212, 220 is equipped with a conventional air filter 240, 241 which eliminates bacteria, viruses, and other particulate matter from entering the blood collection bag when atmospheric pressure is introduced.

The second conduit 141 is bifurcated, by means of a Y-connector or similar device, to provide a separate pathway for blood to each separate blood collection bag 170, 214. Each bifurcation of the conduit 141 is equipped with a shut-off valve 216, 218. In operation, the shut-off valve 218 to the "stand-by bag" 214 is maintained in the closed position to prevent blood from entering into the stand-by bag 214 while blood is being collected in the other blood collection bag 170.

Blood filtering through the system enters into the blood collection bag 170 as a result of the shut-off valve 216 associated with that blood collection bag 170 being in the open position. During collection of blood in the blood collection bag 170, vacuum pressure is applied through vacuum line 210 to blood collection bag 170 only. When the bag 170 has filled with a sufficient amount of blood for infusion, the shut-off valve 216 is closed to prevent entry of any more blood into that blood collection bag 170. The two-way valve 212 is positioned to terminate application of negative pressure to the blood collection bag 170, and atmospheric pressure is thereby produced in the bag. Blood may then be infused to the patient by connecting an infusion line (not shown) to the outlet port 176 of the blood collection bag 170.

During infusion from blood collection bag 170, the shut-off valve 218 associated with the stand-by bag 214 is opened, and blood begins to fill the stand-by bag 214. The two-way valve 220 to the stand-by bag is positioned so that negative pressure is applied to the bag 214.

The blood collection bags 170, 214 are preferably positioned at about five to about six feet above the ground level. If the same amount of negative pressure is applied to both blood collection bags 170, 214 and the emboli filter casing 119, the blood collection bags 170, 214 may be maintained at a height below the emboli filter casing 119. If greater negative pressure is applied to the blood collection bags 170, 214 than is applied to the emboli filter casing 119, aspirated blood will flow from the reservoir 122 to the blood collection bags 170, 214 regardless of the relative height of the bags 170, 214.

It is contemplated by the configuration in FIG. 12 that blood may generally be filtered of excess fluids by a single passage of blood from the reservoir 122 to the blood collection bag 170, 214. However, if it is determined that more fluids need to be removed from the blood, the blood collected in the blood collection bag 170, 214 may be recirculated through the membrane filter 138. For that purpose, a collapsible reservoir bag 224 is provided which connects to the conduit 139, in proximity to the membrane filter 138 by means of a tube 223. A clamp 222 connected to the tube 223 is closed during typical operation to prevent blood from entering the reservoir bag 224. However, when further filtration of fluids is required, the clamp 222 is opened thereby allowing blood to flow into the reservoir bag 224. Blood is urged from the blood collection bag 170, 214 into the reservoir bag 224 by sequentially applying negative pressure and atmospheric pressure to the blood collection bag by manipulation of the two-way valve 212, 220. That is, by producing atmospheric pressure in the blood collection bag, blood is forced from the blood collection bag to the reservoir bag 224. When negative pressure is restored to the blood collection bag, blood will then flow from the reservoir bag 224 back into the blood collection bag. Filtration in the membrane filter 138 takes place with each pass of the blood between the blood collection bag 170, 214 and the reservoir bag 224.

As an alternative to supplying washing fluid to the aspirated blood from the washing fluid bag 130, or when extra washing fluid may be required, washing fluid may be introduced into the blood collection bags 170, 214 at inlet port 226, or may be introduced into the reservoir bag 224 through inlet port 228.

Figure 6:
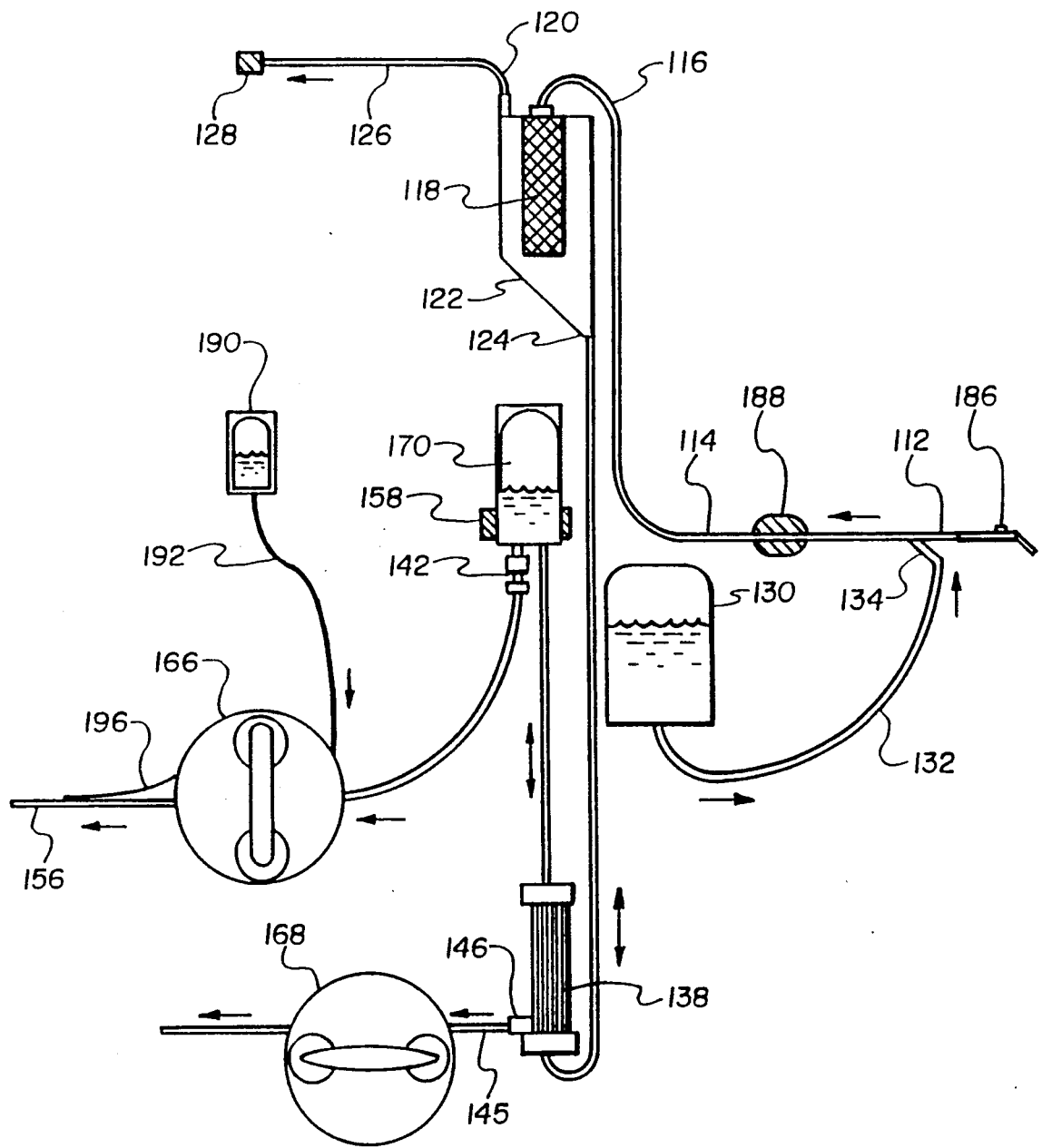
FIG. 6 is a schematic diagram illustrating an alternative embodiment of an intraoperative autotransfusion system.

FIG. 6 illustrates an alternative embodiment of the system described in FIG. 4. It is contemplated that the embodiment of FIG. 6 retains the mobility of the embodiment of FIG. 4 inasmuch as it may be attached to an I.V. pole or similar apparatus. However, the embodiment of FIG. 6 is more mechanized as a result of incorporating into the system a push button control 186 on the suction means 112, an electromagnetic tubing clamp 188 located on the suction tubing 114 which is in electrical communication with the push button control 186, an ultrasonic blood level detector 158 located on the blood collection bag 170, a conductivity monitor 142 at the reinfusion line 156, a blood infusion pump (roller pump) 166, and a filtration pump (roller pump) 168. It is intended that the same relative heights of the components of the apparatus will be maintained as described hereinabove with respect to FIGS. 4, 5 and FIGS. 10 and 12 hereinafter.

When the surgeon wants to aspirate blood from the wound cavity, the pushbutton 186 located on the suction means is activated by the surgeon's thumb pressure. As long as the pushbutton 186 remains activated, the tubing clamp 188 remains open, allowing a mixture of blood and washing fluid to flow into the emboli filter 118. The filtered blood/washing fluid admixture then flows into the blood collection bag 170 by force of gravity via the membrane filter 138.

When there is no bleeding, the push button control 186 remains inactivated. During this period, the tubing clamp 188 located on the suction tubing 114 periodically opens and closes the suction tubing 114 at a predetermined interval (e.g., every one minute). Because of the alternating negative pressure and positive (i.e., atmospheric) pressure in the reservoir 122 due to the closing and opening of the tubing clamp 188, blood is caused to circulate through the membrane filter 138 between the reservoir 122 and the blood collection bag 170. Filtration takes place during this recirculation process.

Filtration in the membrane filter 138 illustrated in FIG. 6 may be enhanced by the association of a filtration pump 168 with the filtration line 145 leading to the filtrate receptacle (not shown). The filtration pump 168 operates at a constant flow rate of about 200 ml/min., as long as two conditions are met: (i) the blood level in the blood collection bag 170 must remain above the level detected by the ultrasonic blood level detector 158, and (ii) the cellular volume fraction as measured by the conductivity monitor 142 must remain below a set value. When these two conditions are not met, the filtration pump 168 will stop.

Conversely, the blood infusion pump 166 will operate at a predetermined constant flow rate when the measured cellular volume fraction, as determined by the conductivity monitor 142, remains above a set value, and the blood level in the blood collection bag 170 remains above the set value as detected by the ultrasonic blood level detector 158.

The embodiment of FIG. 6 further provides a method of neutralizing the anticoagulant (e.g., heparin) present in the blood returning to the patient. The concentration of heparin in the blood can be expected to be about thirty percent of the concentration of heparin in the washing fluid as a result of the filtration process. Substances which selectively neutralize anticoagulants are well known. For example, heparin may be neutralized by protamine. The amount of protamine, or other similar neutralizing substance, in the neutralizer retainer means 190 is predetermined by the amount of anticoagulant which is originally placed in the washing fluid, and by the expected concentration of anticoagulant in the blood. The anticoagulant neutralizer solution retained in the retainer means 190 is fed into the reinfusion line 156 by way of a neutralizer feed line 192. The neutralizer is fed into the reinfusion line 156 at a rate equal to the reinfusion rate of the blood. This may be accomplished by providing a two channel roller pump 166 instead of a single channel roller pump. One channel may be used for blood reinfusion and the other channel for the neutralizer. The ratio between the blood and the neutralizer flow rates may be varied by using different tubing sizes for the blood reinfusion line 156 and the neutralizer feed line 192.

Figure 7:
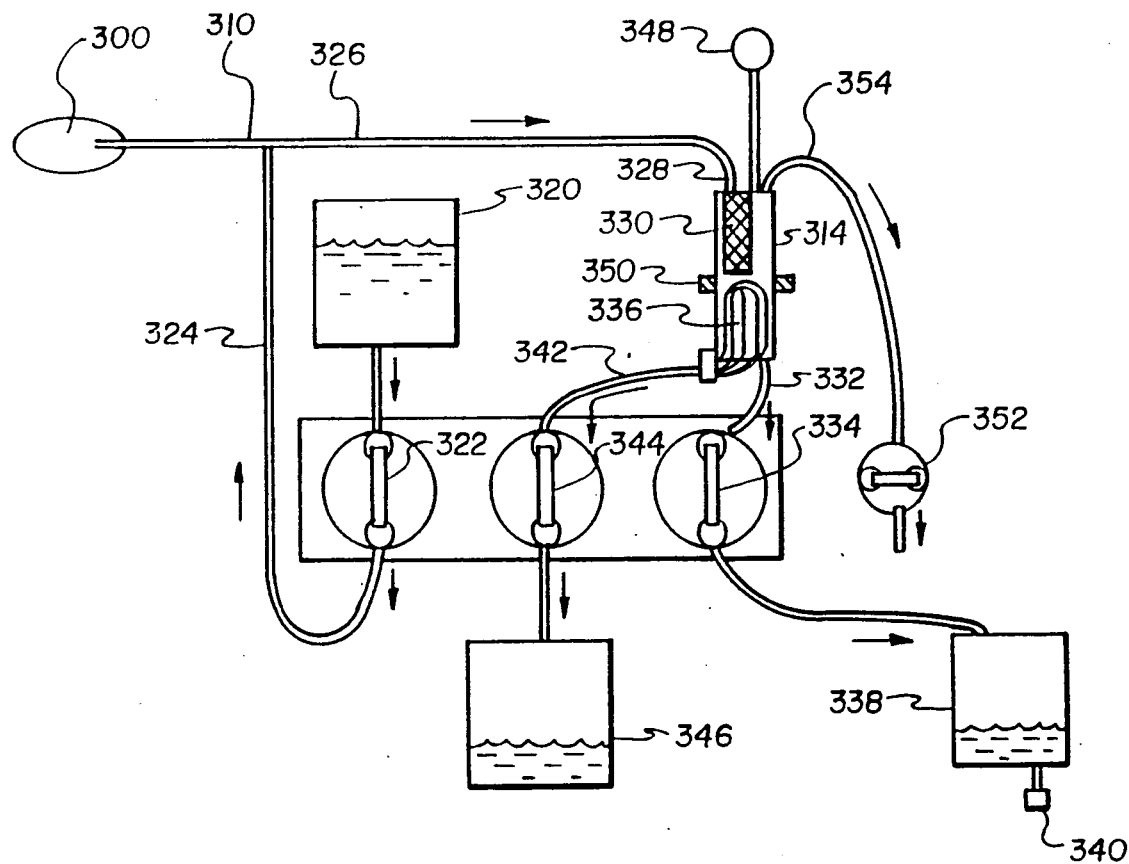
FIG. 7 is a schematic diagram illustrating a postsurgical autotransfusion system.
Figure 8A:
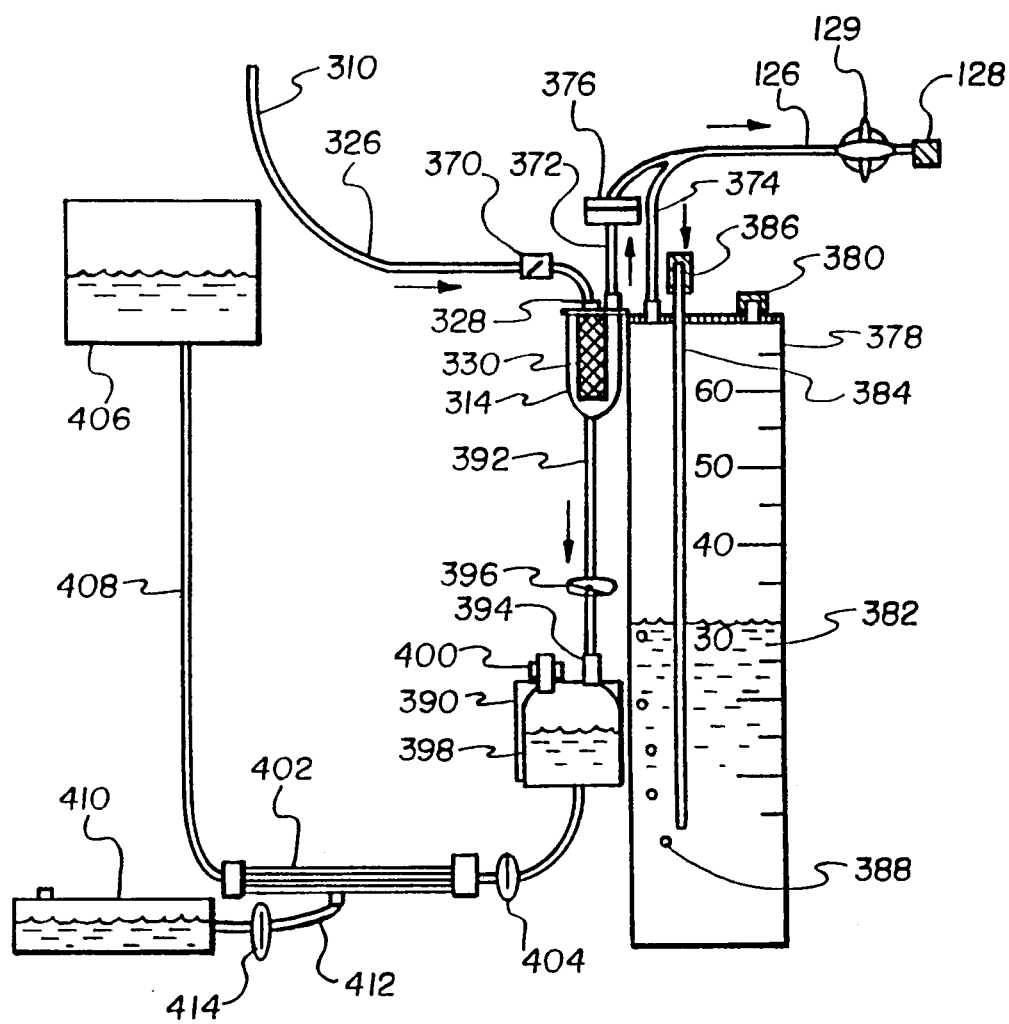
FIG. 8-A is a schematic diagram of a machineless postsurgical autotransfusion system using a water-manometer for vacuum regulation.
Figure 8B:
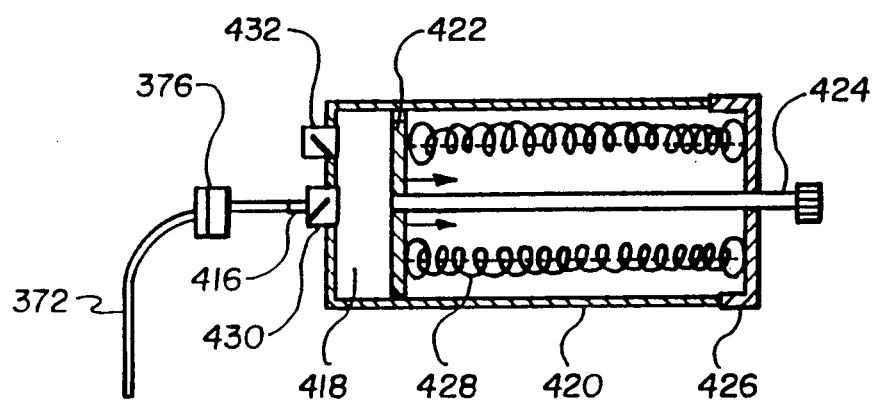

The embodiments illustrated in FIGS. 7 and 8 are embodiments which are designed for use post-surgically. That is, they are designed to aspirate blood from a closed wound site into which has been placed a drainage tube in expectation of postoperative bleeding. In FIG. 7, the closed wound site is generally designated at 300. The closed wound site may be located anywhere where surgery has been performed on the body including the pleural cavity, chest cavity or abdomen. Drainage tubing 310 has been inserted at the closed wound site by the surgeon in order to drain out any blood.

The embodiment in FIG. 7 is designed to provide a controlled amount of washing fluid to the drainage tubing, or it may be injected into the closed wound site using a double lumen chest drainage tubing. Washing fluid contained in washing fluid bag 320 may or may not contain anticoagulant. For example, mediastinal blood is reported to be free of fibrinogen, a main ingredient of blood clots and anticoagulant may not be necessary as a result. Washing fluid is pumped from the washing fluid bag 320 by pump means 322, such as a roller pump. The washing fluid is urged thereby into the drainage tubing 310, or into the closed wound site 300 if a double lumen drainage tube is used, through the washing fluid line 324 at a controlled rate.

The aspirated blood is mixed with the washing fluid in the suction tubing 326. Alternatively, the blood and washing fluid which is admixed at the wound site is aspirated into the suction tubing 326. The suction tubing 326 terminates at the inlet port 328 of emboli filter 330. The aspirated blood which is diluted with washing fluid is filtered through the emboli filter 330 to remove large particulates and air bubbles from the blood. As illustrated in FIG. 7, the emboli filter may be configured with a membrane filter 336 as an integrated unit, or cascade filter, as previously described with respect to FIG. 3.

The blood level in the reservoir 314 is maintained above a pre-set limit by monitoring the blood level using an ultrasonic air detector 350. If the blood level falls below the level of the ultrasonic air detector 350, an air vent pump 352 connected to a vent line 354 exiting the reservoir 314 is activated to pump out air from the reservoir 314. The air vent pump 352 is only activated when the blood level falls below the pre-set limit. This procedure prevents air from being introduced into the filtered blood.

Blood which has been filtered through the emboli filter 330 is then filtered through a membrane filter 336 which is located beneath the emboli filter 330 as part of an integral unit. The embodiment of FIG. 7 illustrates employment of the same integrated "cascade" filter which is illustrated in FIG. 3. Washing fluid and other excess fluids are separated from the blood by the membrane filter 336. The filtrate is drained into the filtrate receptacle 346 by means of the filtration line 342. Filtrate exiting from the membrane filter 336 may be drawn by a filtrate pump 344 so that the filtrate may be collected in the filtrate receptacle 346. During the membrane filtration process, the washing fluid that was injected into the drainage tubing 310 or closed wound site 300 will be removed from the blood. The filtrate may also contain other impurities present in the blood such as activated coagulation factors, plasma hemoglobin, fibrin degradation products, and lipids. The membrane filter 336 may have a pore size cut-off ranging from 40,000 daltons to a few millions of daltons depending upon the size of impurities to be removed from the blood.

The volume of filtrate removed and the volume of washing fluid injected into blood may be roughly equalized by operating the washing fluid pump 322 and filtrate pump 344 at the same speed, and using the same diameter of tubing for the washing fluid line 324 and the filtrate line 342.

Filtered blood exits from the integrated membrane filter 336 and is carried via a conduit 332 to the blood collection bag 338. Movement of filtered blood through the conduit 332, and ultimately the rate of reinfusion, is accomplished by operation of the reinfusion pump 334. When a suitable amount of blood is collected in the blood collection bag 338, it may be reinfused to the patient, by gravity flow, by attaching a second receptacle (not shown) to the port 340 of the blood collection bag 338 without detaching the blood collection bag 338 from the apparatus. The second receptacle is positioned at a height above the patient suitable for obtaining gravity flow from the second receptacle into the patient. A filter (not shown) having an approximate pore size of 40 microns may be interconnected between the blood collection bag 338 and the second receptacle for further filtration of the blood prior to reinfusion. Alternatively, the filtered blood collected in the blood collection bag 338 may be continuously reinfused to the patient by connecting a reinfusion line to the port 340.

When the three roller pumps 322, 334, 344, which are driven by a single motor and gear unit (i.e., it may be referred to as a three channel roller pump), are operated at the same speed, the flow rates of washing fluid through the washing fluid pump 322 and that of filtrate through the filtrate pump 344 may be made to be exactly equal. At the same time, the flow rate through the reinfusion pump 334 may be made equal to the bleeding rate.

Bleeding rate in the closed wound site varies with time. The embodiment illustrated in FIG. 7 is capable of determining the transient variation of bleeding rate and can process the blood accordingly. Because the washing fluid pump 332 and the filtrate pump 344 operate at the same speed, negative pressure is automatically created in the closed wound site 300 by operation of the reinfusion pump 334. Negative pressure induces the mixture of aspirated blood and washing fluid to flow towards the emboli filter 330. The magnitude of the negative pressure is proportional to the speed of the reinfusion pump 334 and inversely proportional to the bleeding rate. It is known in the art that the negative pressure must be kept below −20 cm of water. A negative pressure sensor and pressure control unit 348 may be provided in order to control the negative pressure in the drainage tube 310 around −20 cm of water.

When the bleeding in the closed wound site 300 decreases, the negative pressure may exceed the set maximum value (e.g. −20 cm water), and the speed of the reinfusion pump 334 is accordingly reduced by the control unit 348 until the measured pressure remains below the maximum value. It should be noted that when the speed of the reinfusion pump 334 is reduced, the speeds of the other pumps 322 and 344 will be reduced proportionately since they are powered by the same motor and gear unit.

If bleeding in the closed wound site 300 increases, the negative pressure in the drainage tube 310 decreases below the set value (i.e., −20 cm of water), and the pressure control unit 348 accordingly increases the pump speed until the negative pressure approaches the set value. By this control mechanism, all the pump speeds (reinfusion pump 334, washing fluid pump 322, and filtrate pump 344) are automatically adjusted to the bleeding rate, while keeping the negative pressure in the drainage tube within the safe value of −20 cm of water.

It will be appreciated that blood does not come in contact with air during the aspiration process described above thereby totally eliminating blood-air interaction and protein denaturation. The blood-air interface is completely eliminated in the apparatus by flushing it with normal saline or Ringer's solution before attaching the apparatus to the drainage tube at the wound site. Also, because the blood collection bag 338 is a conventional collapsible plastic bag into which vacuum has been applied during its sterilization, no air comes in contact with the blood. It will be appreciated that the elimination of blood-air interface minimizes protein denaturation and eliminates potential dangers of air emboli.

The embodiment of FIG. 8-A presents an alternative embodiment of the invention for use post-surgically. The illustrated embodiment does not depend upon any capital equipment (i.e., pumps, transducers, sensors, electronic controllers and microprocessors), but is dependent only upon a conventional vacuum source available in any operating room, surgical unit or post-surgical management unit (e.g., intensive care unit).

As shown in FIG. 8-A, blood is aspirated from the closed wound site via the drainage tubing 310 under accurately controlled negative pressure. The drainage tubing 310 integrates with suction tubing 326 which terminates at the inlet port 328 of a conventional emboli filter 330. A conventional one-way valve, such as a flap valve 370 may be provided in the suction tubing 326 in order to prevent reverse flow of blood or air to the closed wound site in case of accidental failure of the vacuum source.

The vent line 126 is connected to an emboli filter vent line 372 which is in turn connected to the reservoir 314 associated with the emboli filter 330. The vent line 126 is connected to a vacuum source 128. The amount of vacuum may be regulated, in part, by regulator valve means, such as a conventional water-manometer 378, as shown. The vent line 126 is connected to water-manometer line 374 to interconnect the water-manometer to the vacuum source. A microporous filter 376 of approximately 0.8 micron pore size (e.g., as made by Millipore Corp., MA.) is associated with the emboli filter vent line 372 in order to prevent transfer of bacteria or viruses into the emboli filter from the vent line 126 in case of accidental failure of the vacuum source 128.

A conventional water-manometer 378 is used in this embodiment to accurately control the required negative pressure in the vent line 126. The water manometer may comprise a graduated tubular or rectangular transparent plastic container 378 about 70 cm high with a sealed cap at its top end. This cap may be provided with at least three ports: one port provides a point of connection to the water-manometer line 374; a second port 380, originally sealed by standard sterile technique, is used thereafter for filling the container 378 with sterile saline solution 382 to the required height within the container 378; and a third port is used for inserting a bubbler 384 into the container 378. The bubbler 384 is a long rigid transparent plastic tube the top open end of which is filled with sterile cotton gauze 386, and the bottom open end of which remains about one cm above the bottom of the container 378.

The height of water or saline solution 382 in the container 378 determines exactly the negative pressure in the water-manometer line 374, and the vent line 126, provided the vacuum regulator valve 129 is adjusted so that a continuous series of air bubbles 388 appear at the lower end of the bubbler 384 in the saline solution 382. When the vacuum regulator valve 129 is adjusted such that the negative pressure in the vent line 126 is slightly greater than the height of liquid 382 in the container 378, air will be sucked through the cotton gauze 386 (or a 0.8 microporous filter), through the bubbler 384, through the water or saline solution 382, and vented out by the water-manometer line 374 and vent line 126. If the negative pressure in the vent line 126 is less than the height of the water or saline column 382 in the container 378, air bubbles 388 will not appear in the water or saline 382. In such a case, the vacuum regulator valve 129 should be readjusted to increase the vacuum until a series of bubbles 388 are seen in the water or saline 382.

The amount of negative pressure applied to the emboli filter can be regulated by any other appropriate means. Another alternative means, illustrated in FIG. 8-B, is a piston-like system comprising a hollow cylindrical outer body 420 in which is slideably disposed a flattened disk 422 connected to a plunger 424. The cylindrical body 428 has a forward end with an aperture 416 to which is connected the emboli filter vent line 372. The cylindrical outer body 428 has a rearward end 426 through which the plunger 424 passes. A plurality of springs 428 are interconnected between the disk 422 and the rearward end 426 of the cylindrical outer body. The circumference of the disk is substantially equal to the circumference of the inner cylindrical body, and fits snugly therewithin. When relaxed, the springs force the disk to the rearward end 426 of the cylindrical outer body 420. In operation, once the vacuum source is applying negative pressure to the emboli filter, the plunger 424 is forced toward the forward end of the cylindrical outer body 420, and the springs become distended. As the disk 422 is urged to the forward end, a first one-way flap valve 430 is closed by the compression building in the chamber 418. Concurrently, a second one-way flap valve 432 opens to allow air to escape the chamber 418. The exuded air is, therefore, not urged into the wound site. Negative pressure is then produced in the chamber 418 of the cylindrical outer body 420. When the pressure in the chamber 418 is less than the atmospheric pressure, the valve 432 closes and the valve 430 opens, drawing air from the vent line. Since the wound site is closed, the movement of piston 422 away from the inlet port (or the expansion of the chamber 418) creates a negative pressure in the closed wound site, which in turn will induce draining of shed blood from the wound site via the drainage tubing 310 into the collection bag 390. The magnitude of negative pressure created in the chamber is proportional to the number of springs interconnected between the disk and the cylindrical outer body, the tension achieved by each spring, and the volume of the chamber. The negative pressure is inversely proportional to the friction between the disk 422 and the inner wall of the cylindrical outer body 420, and the total volume of the closed wound site, plus the drainage tubing 310 and the volume of the components of the system (emboli filter, membrane filter, bags and tubings).

A filter 376 (i.e., a 0.8 micrometer filter from Millipore Corp., MA.) may be attached to the emboli filter vent line 372 proximate the cylindrical outer body 420 to prevent the transfer of bacteria, viruses, or other harmful agents into the emboli filter vent line 372.

Blood aspirated into suction tubing 326 is directed through the emboli filter 330. The emboli filter used in this embodiment may be any of those previously described in other embodiments. The blood flows by gravity from the emboli filter 330 into the reservoir 314, and into the blood collection bag 390 through a vertical conduit 392. The vertical conduit 392 should be at least two feet in length to facilitate draining of blood from the reservoir 314 to the blood collection bag 390 by gravity. Such length is also required to overcome the force of negative pressure applied at the emboli filter vent line 372. The bag 390 may contain a precalculated amount of anticoagulant to prevent clotting of blood accumulated in the blood collection bag 390. The vertical conduit 392 is connected to the blood collection bag 390 by a standard connector means 394 (e.g., leur lock). A clamp 396 may be provided to close the conduit 392 under appropriate conditions described below.

When the blood collection bag 390 becomes almost full with blood 398, the conduit 392 is closed with the clamp 396. Under emergency situations when the patient needs blood immediately, as determined by the physician, the blood collection bag 390 may be easily disconnected from the connector means 394. A fresh sterile blood collection bag may then be attached to the connector means 394 under sterile conditions. The blood collected in the blood collection bag 390 may be reinfused to the patient by attaching a reinfusion line to the infusion port 400 of the blood collection bag 390 and by applying a pressure cuff to the bag. Reinfusion of the blood following filtration through the emboli filter 330 only may be appropriate where immediate reinfusion is necessary to the maintenance of the patient.

Alternatively and preferentially, the blood may be mixed with washing fluid and filtered further. Similar to the embodiment described in FIG. 5, washing fluid may be introduced into the blood in the blood collection bag 390 by securing clamp 396, removing clamp 404 on the tubing interconnected between the blood collection bag 390 and the membrane filter 402, securing clamp 414 on the filtration line 412, and by manipulating the height of the washing fluid bag 406 in relation to the blood collection bag 390. That is, the washing fluid bag 406 should be sequentially raised and lowered above or below the level of the blood collection bag 390 in order to urge washing fluid from the washing fluid line 408 through the membrane filter 402 and into the blood collection bag 390. Alternatively, the washing fluid retainer may be connected to a mechanical device which would sequentially raise and lower the washing fluid 406.

When the washing fluid has been mixed sufficiently with the blood, the clamp 414 on the filtration line 412 is opened. The circulation of the blood and washing fluid admixture from the blood collection bag 390 and the washing fluid bag 406 continues, and as the admixture passes through the membrane filter 402, excess fluid and other matter is filtered off through the filtration line 412 into the filtrate receptacle 410. When the amount of fluid in the filtrate receptacle 410 is roughly equal to the amount of washing fluid originally admixed with the blood, the clamp 414 is replaced on the filtration line 412 to prevent further filtration. Blood is urged back into the blood collection bag 390 by raising the washing fluid bag 406 above the level of the blood collection bag 390. When the blood has completely filled the blood collection bag 390 again, the clamp 404 is replaced on the tubing exiting the collection bag, and reinfusion may begin. The blood may be reinfused by attaching a reinfusion line to the port 400 of the blood collection bag 390 and applying a pressure cuff to the bag 390.

The embodiment of FIG. 8-A provides a simple, inexpensive on-line method of purification and drainage of the blood from the emboli filter by providing adequate negative pressure and hydrostatic pressure so that the purified blood can be collected in a conventional blood collection bag for reinfusion purposes.

Figure 13:
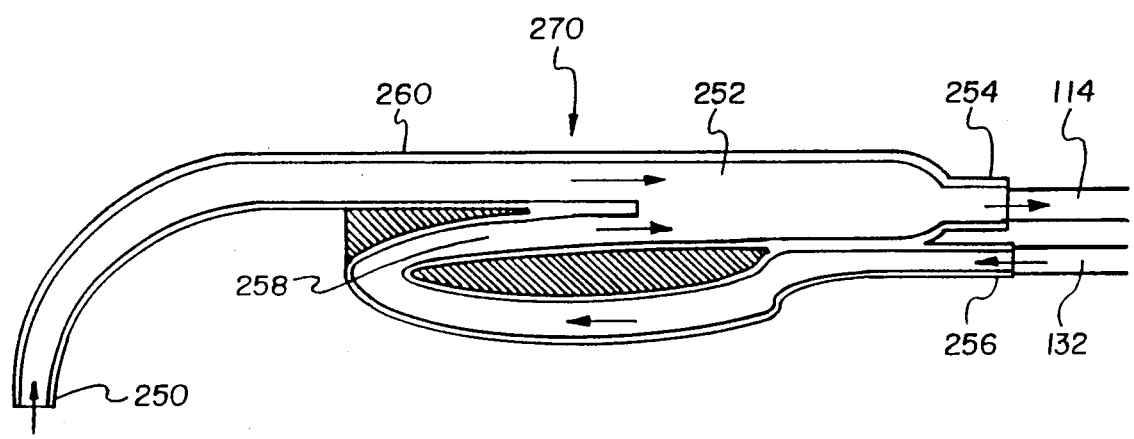
FIG. 13 is a cross-sectional view of a suction means for use in the invention.

In these embodiments where washing fluid with anticoagulant is admixed with aspirated blood prior to aspiration into the emboli filter (FIGS. 1, 2, 3, 4, 6, 7 and 12), a specialized suction means 112 may be used where the washing fluid is delivered into the handle of the suction means. Delivery of washing fluid into the suction means has the advantage of providing for more complete admixture, and for less clogging in the suction tubing 114 due to coagulation of blood in the tubing prior to admixture with the washing fluid. FIG. 13 illustrates a preferred suction means, generally at 270.

Suction tubing 114 is connected to the suction means 270 at connector point 254, and is connected at its other end (not shown) to the emboli filter. The washing fluid line 132 is connected to the suction means 270 at connector point 256, and is connected at its other end (not shown) to the washing fluid bag. As blood is aspirated through the open tip 250 of the suction means 270, negative pressure increases to about 120 mm Hg. As a result, washing fluid from the washing fluid bag, which is maintained approximately two feet below the suction means 270, is drawn into washing fluid line 132. The washing fluid enters into the loop 258 of the suction means 270, and thereby achieves a 180° change in direction of flow. The resulting flow of washing fluid exiting from loop 258 is parallel to, and in the same direction as, the blood being aspirated through the tip 250. It is only because the aspirated blood and washing fluid are caused to flow in the same direction as a result of this configuration that washing fluid is aspirated in equal proportion to the amount of blood aspirated. The blood and washing fluid are admixed in chamber 252 of the suction means 270, and the admixture is carried to the emboli filter (not shown) via suction tubing 114.

During surgery, it may occasionally occur that tissues or other matter block the suction tip 250. If that were to occur, the increased negative pressure would cause washing fluid alone to be aspirated into the emboli filter while no blood is being aspirated. To prevent the aspiration of washing fluid during periods of time when there is no bleeding in the would site (i.e., no blood is being aspirated), and the suction tip 250 is blocked, an aperture 260 may be provided in the suction means 270 so that air will enter the suction means 270 and reduce the negative pressure. The reduced negative pressure will prevent washing fluid from being aspirated into the suction means 270 and the suction tubing 114. During normal operation, when the suction tip 250 is unblocked, the aperture is to be covered by the surgeon's or user's thumb, finger, or hand. Covering the aperture will allow normal increase in the negative pressure to achieve proper aspiration.

The suction means may be made of any suitable material, but is may be preferred to use a transparent material for the suction tip 250 in order to monitor the occurrence of clogging at the tip.

OPERATION OF THE INVENTION

Referring to FIG. 1, blood is aspirated from the open wound site 10 by the suction means 12. Aspirated blood flows through the suction tubing 14 towards the emboli filter 18. Due to the increased negative pressure in the suction tubing 14, heparinized washing fluid contained in the washing fluid bag 30 is infused through the washing fluid line 32 into the suction tubing 14 at 34 in proportion to the blood flow rate. Thus, the invention provides a mechanism by which washing fluid can be injected into the system in proportion to the aspiration of shed blood without using any pump or control units. A mixture of blood, heparinized washing fluid and some air is drawn into the emboli filter 18 where it is degassified and filtered to remove particles larger than 40 microns. Filtered blood which is free of air emboli is collected in the reservoir 22. Air separated from the blood is vented through the vent line 26 connected to a controlled vacuum source 28.

Blood is drawn from the reservoir 22 by the recirculation pump 36 and circulates through a membrane filter 38, a flow constrictor 40, a hematocrit monitor 42, a recirculation valve 44, and back into the reservoir 22 to be circulated again. It should be noted that the venous valve 54 remains closed as long as the recirculation valve 44 remains open. Filtrate leaving the filtrate port 46 is collected in a filtrate receptacle 48. The filtrate typically contains activated coagulation factors, plasma-free hemoglobin, washing fluid, and other impurities which are below the molecular weight cut off of the membrane filter. Recirculation continues until an adequate amount of fluid is removed from the blood by the membrane filter 38 as indicated by the hematocrit monitor 42. When the hematocrit of the blood at the outlet of the membrane filter 38 reaches a set value, the recirculation valve 44 closes and the blood is directed to the reinfusion line 56 through the venous filter 52, with simultaneous opening of the venous valve 54.

To ensure that no air emboli will be infused with the blood into the patient, and to ensure that no blood having a cellular volume fraction less than the specified value will be reinfused, the invention provides three conditions which must be met in order for the venous valve 54 to open. These three conditions are: (i) cellular volume fraction of the blood as measured by the conductivity monitor should be at least equal to a set value (e.g., 35%); (ii) venous blood should be free of air emboli as monitored by the ultrasonic detector 58; and (iii) the level of blood in the reservoir 22 should be above the minimum level as monitored by the blood level detector 60.

Should the level of blood in the reservoir 22 fall below the minimum limit as measured by the blood level detector 60, the filtrate valve 62 located in the filtration line 45 will close along with the venous valve 54 to prevent a further fall in the blood level in the reservoir 22.

The invention provides a mechanism by which the filtration rate and the processing of blood can be varied in proportion to the variation in bleeding rate. This is accomplished by varying the speed of the recirculation pump 36 in proportion to the variation in bleeding rate. The recirculation pump 36 may be set to run at a minimum speed corresponding to 100 ml/min when the blood in the reservoir 22 remains below the blood level detector 64. When the bleeding rate increases, the level of blood in the reservoir 22 will rise from the low level detected by the blood level detector 60 to upper level detected by the detector blood level 64. When the blood level rises above the upper level, the speed of the recirculation pump 36 increases gradually until the level of blood falls below the upper level.

Referring to FIG. 3, blood is aspirated from the open wound site by the suction means 112, induced by the controlled vacuum from the vacuum source 128 applied via the vent line 126. Aspirated blood is mixed, in the suction tubing 114, with the washing fluid from the washing fluid bag 130 in proportion to the suction rate of the blood as described above. Diluted blood enters into the integrated filter, or integrated cascade filter, which comprises an emboli filter 118 and membrane filter 138. Air emboli are first removed by the emboli filter 118 along with other macroparticles above 40 microns in size. The filtered blood is then collected in the reservoir 122 where it is subjected to membrane filtration by the membrane filter 138. Membrane filtration is induced by the filtration pump 168 which runs at a constant speed. However, when the level of blood in the reservoir 122 falls below a set limit as detected by the blood level detector 160, or when the cellular volume fraction of blood is above the set limit as measured by the conductivity monitor 142, the filtration pump 168 will stop.

When the measured cellular volume fraction (hematocrit level) of blood becomes equal to or greater than the set value, the infusion pump 166 is reactivated to return the processed blood to the patient via the reinfusion line 156; however, the level of blood in the reservoir 122 must remain above the set limit as detected by the blood level detector 160 to avoid air being sucked into the system.

The embodiment of the invention illustrated in FIG. 4 presents a significantly simplified version of the system in which all components are totally disposable, and which operates without the use of any roller pumps, ultrasonic bubble detectors, valves, and other control units. The only equipment required is a controlled vacuum source. The embodiment of the invention is adaptable to an I.V. pole.

When there is bleeding in the open wound site, blood will be aspirated into the emboli filter 118 through the suction tubing 114. Filtered blood flows out of the emboli filter 118, into the reservoir 122, and through the membrane filter 138 into the blood collection bag 170 by gravity flow. Membrane filtration takes place as the blood passes through the membrane filter 138. Controlled negative pressure 172 may be applied to the filtrate receptacle 148 by means of a vacuum source 172 attached to a vacuum line 174 in order to increase filtration rate.

Due to the increased negative pressure in the reservoir 122 as blood is being aspirated, blood is lifted from the blood collection bag 170 to the reservoir 122 through the membrane filter 138. Membrane filtration takes place during this period.

Prior to reinfusion of blood from the blood collection bag 170, the volume of filtrate collected in the filtrate receptacle 148 should be compared to the volume of washing fluid injected into the suction tubing 114 to assure that most of the fluid has been removed from the blood. Since both the washing fluid bag 130 and the filtrate receptacle 148 are calibrated, the volume of washing fluid consumed and the volume of filtrate collected will be easily determined. If more fluid needs to be removed from the blood, an attending medical person will periodically open and close the suction tubing 114 at point AA (see FIG. 4) every 3 to 5 minutes in order to maintain a blood flow back and forth between the blood collection bag 170 and the reservoir 122. During this process, further membrane filtration takes place.

When an adequate amount of fluid is removed from the blood and a sufficient amount of blood is collected in the blood collection bag 170, the blood can be reinfused to the patient by gravity flow of the blood through port 176 of the blood collection bag 170.

The embodiment illustrated in FIG. 5 differs in operation from the embodiment shown in FIG. 4 only by the relative placement of the blood collection bag 170 to the washing fluid retainer means 130 and the membrane filter 138. In this embodiment, aspirated blood enters into the emboli filter 118 and flows by gravity into the blood collection bag 170. A tubing clamp 182 located below the blood collection bag prevents blood from exiting the bag 170. When the blood collection bag 170 is full, the blood may be reinfused to the patient immediately when the medical condition requires. Alternatively, the blood may be reinfused to the patient by attaching a reinfusion line to port 176 and placing a pressure cuff on the blood collection bag 170.

If further purification of the blood is desired or required, the tubing clamp 182 is removed from the tubing 178 interconnected between the blood collection bag 170 and the membrane filter 138, the filtration line tube clamp 184 is secured, and washing fluid from the washing fluid bag 130 on the filtration line 145 is allowed to flow through the membrane filter 138 toward the blood collection bag 170. Admixture of blood and washing fluid is thereby accomplished. When the filtration line tubing clamp 182 is removed, filtration takes place. The filtrate, containing washing fluid, activated coagulation factors, free hemoglobin and other impurities, flows into the filtrate receptacle 148. As described above, a vacuum force may be applied to the filtrate receptacle 148 by a vacuum source 172 to increase filtration.

As described above, pressure may be intermittently applied at point AA of the suction tubing 114 to urge recirculation of the blood/washing fluid admixture through the membrane filter 138. When a sufficient amount of fluid has been removed and collected in the filtrate receptacle 148, the blood may be urged into the blood collection bag 170 or into the washing fluid retainer means 130. The blood may then be reinfused to the patient from the port 176 of the blood collection bag 170 or through the port 133 of the washing fluid bag 130 by attaching a reinfusion line thereto.

Referring to FIG. 6, when the surgeon wants to aspirate blood from the wound site, the pushbutton 186 located on the handle of the suction means 112 is activated by the surgeon's thumb pressure. As long as the pushbutton 186 remains activated, the tubing clamp 188 on suction tubing 114 remains open, allowing a mixture of blood and washing fluid to flow into the emboli filter 118. The filtered blood then flows into the blood collection bag 170 through the membrane filter 138.

However, when there is no bleeding, the pushbutton 186 remains inactivated. During this period, the tubing clamp 188 located on the suction tubing 114 periodically opens and closes the suction tubing 114 at a predetermined interval (e.g., every one minute). Because of the alternating negative and positive (i.e., atmospheric) pressure in the reservoir 122 due to the closing and opening of the clamp 188, blood is circulated through the membrane filter 138 between the reservoir 122 and blood collection bag 170. Filtration takes place during this process.

Filtration in the membrane filter 138 is achieved by the filtration pump 168, which may operate at a constant flow rate of 200 ml/min., as long as two conditions are met: (i) the blood level in the blood collection bag 170 remains above the level detected by the ultrasonic blood level detector 158, and (ii) the cellular volume fraction as measured by the conductivity monitor 142 remains below a set value. When these two conditions are not met, the filtration pump 168 will stop. Similarly, when the blood level remains above the level as detected by the blood level detector 158 and the cellular volume fraction remains above the set value, the blood infusion pump 166 will operate at a predetermined constant flow rate; but the infusion pump 166 will stop when the two conditions are not met.

The embodiment in FIG. 6 also provides a means for neutralizing any anticoagulant that was mixed with the washing fluid prior to reinfusion of the blood into the patient. The neutralizing substance, such as protamine, is retained in the neutralizer retainer means 190. A specific amount of neutralizer, the concentration of which has been predetermined by the amount and concentration of anticoagulant placed in the washing fluid, is fed into the reinfusion line 156 by the infusion pump 166 which is designed to have two channels therein.

The embodiments and methods of operation described above are those directed to use during surgery. the embodiments disclosed in FIGS. 7 and 8, however, are those which are used post-surgically to aspirate and filter blood from a closed wound site which has a drainage tube implanted therein.

In FIG. 7, blood from the closed wound site 300 is drawn by the reinfusion pump 334 at a controlled negative pressure through the drainage tubing 310, suction tubing 326, and emboli filter 330. The washing fluid pump 322 infuses washing fluid from the washing fluid bag 320 into the suction tubing 326. Alternatively, the washing fluid pump 322 may infuse washing fluid into the closed wound site 300 at a rate proportional to the bleeding rate.

The blood level in the reservoir 314 is always maintained above the limit detected by the ultrasonic air detector 350, which activates the air vent pump 352 to pump out air from the emboli filter 330 only when the blood level falls below the set limit.

Filtered blood free of particulates larger than 40 microns is then subjected to membrane filtration by the membrane filter 336. Whatever fluid is added to the blood will be removed as filtrate by the membrane filter 336. This filtrate typically contains activated coagulation factors and other impurities which are below the molecular weight cut off of the membrane filter. A plasma filter with a molecular weight cut off of a few million daltons or an ultrafilter with a molecular weight cut off of about 40,000 to 400,000 daltons can be chosen as required. The filtered blood is drawn from the integrated cascade filter by the reinfusion pump 334, and is collected in the blood collection bag 338.

The embodiment in FIG. 7 provides a means of exactly balancing the filtration rate to the washing fluid infusion rate, and exactly varying the washing fluid infusion rate in proportion to the bleeding rate in the closed wound site, while maintaining the negative pressure in the closed wound site within safe limits (e.g., below −20 cm of water). This is achieved by employing a three channel roller pump (comprising 322, 344, 334) driven by a single motor and gear unit, and employing a pressure control unit 348. The pumping rates of the washing fluid pump 322 and the filtrate pump 344 are exactly balanced to each other. Concurrently, the flow rate of the reinfusion pump 334 is kept equal to the bleeding rate by the negative pressure control unit 348. The pressure sensor and control unit 348 associated with the emboli filter 330 increases or decreases the pump speed depending upon whether the negative pressure decreases or increases around a set value (e.g., −20 cm of water). Purified blood may be reinfused to the patient through the port 340 of the blood collection bag 338, either intermittently in batches by gravity flow, or continuously on a real time basis.

The embodiment of FIG. 8-A, which is also used post-surgically, provides a very simple, inexpensive, and disposable system, not dependent upon any capital equipment. Blood flows from the closed wound site via the drainage tubing 310 into the suction tubing 326. Blood flows through the one-way valve 370 to the blood inlet port 328 of the emboli filter 330. Aspiration is induced by the negative pressure created by the vacuum line 126, and is approximately controlled by the vacuum regulator valve 129. The negative pressure is accurately controlled by the water-manometer 378. The height of liquid 382 injected into the water-manometer 378 via the sealed port 380 determines the exact negative pressure in the water-manometer line 374 and vent line 126. The vacuum regulator valve 129 is adjusted so that a series of bubbles 388 continuously appear in the liquid column 382. Alternatively, a piston or other means may be used to regulate the negative pressure.

The filtered blood flows down by force of gravity from the reservoir 314 associated with the emboli filter 330 to the blood collection bag 390 via conduit 392 which provides adequate hydrostatic pressure for the blood to flow into the blood collection bag 390. When the bag 390 becomes almost full with filtered blood 398, the conduit 392 is closed with a clamp 396, the blood collection bag 390 is disconnected from the connector means 394, and a fresh sterile blood collection bag is attached to the connector means 394 under sterile conditions. The blood collection bag 390 containing the filtered blood may be suspended from an I.V. pole, and the blood may be reinfused to the patient via the infusion port 400 of the blood collection bag 390. During reinfusion, another conventional emboli filter (e.g., Pall filter) may be used in the reinfusion line to prevent transfer of any blood clots to the patient.

Alternatively, the blood collected in the blood collection bag 390 may be mixed with washing fluid and filtered further. Admixing occurs when the clamp 404 on the tubing interconnected between the blood collection bag 390 and the membrane filter 402 is removed and washing fluid from the washing fluid bag 406 is allowed to flow into the blood collection bag 390. By raising and lowering the height of the washing fluid bag 406 relative to the blood collection bag 390, the admixture of blood and washing fluid can be made to circulate continuously through the membrane filter 402 which is located therebetween. Filtration occurs when clamp 414 located on the filtration line 412 is removed thereby allowing filtrate to be drawn off into the filtrate receptacle 410. When a sufficient amount of filtrate has been removed, the washing fluid bag 406 is once again raised above the level of the blood collection bag 390 to cause the blood to flow into the latter. Clamp 404 is then replaced to prevent blood escaping from the blood collection bag 390. Reinfusion may begin as described above.

The simplified embodiment illustrated in FIGS. 10 and 11 is configured to allow immediate transfusion of membrane filtered blood while blood collection continues. It is contemplated that the embodiment of FIG. 10 is attached to an I.V. pole or similar device. While the components of the embodiment function in the same manner as described above, the position of the components in relation to each other allows blood to be infused on a constant, real-time basis. That is, the emboli filter casing 119 should be kept at least six feet above the ground, and the membrane filter 138 should remain at or about ground level. Because the negative pressure applied by the vacuum source 128 (−120 mm Hg) can only raise blood 5.04 feet, the amount of blood collecting in the reservoir 122, coupled with the length of the conduit 139, allows blood to constantly flow downwardly through the conduit 139. Thus, blood is constantly being filtered through the membrane filter 138 and can be reinfused to the patient from the blood collection bag 170 through the infusion port 176. While infusion is taking place from the blood collection bag 170, a second blood collection bag is attached to the connector 198 for further blood collection.

The filtered blood can also be cell-washed by mixing the blood with washing fluid. Washing fluid is contained or placed in the blood collection bag 170. By raising and lowering the height of the blood collection bag 170 relative to the membrane filter 138, blood is forced between the blood collection bag 170 and the conduit 139 which results in admixture of blood in the conduit with washing fluid. During the admixing procedure, a clamp 184 remains on the filtration line 145 to prevent premature filtration. When admixture is complete, the clamp 184 is removed from the filtration line 145 and filtration begins. Admixture can take place even while blood collection is occurring.

The embodiment of FIG. 12 presents a further means of collecting and infusing blood on a constant, real-time basis which does not require manipulation of the blood collection bag 170. Rather, the blood collection bag 170 and the filtrate receptacle 148 are connected to the same vacuum source 128 to which the emboli filter casing 119 is attached. Negative pressure applied to the blood collection bag 170 enhances blood collection, and negative pressure applied to the filtrate receptacle 148 enhances filtration. Because the filtrate receptacle 148 is attached to the same vacuum source 128 as the emboli filter casing 119, when negative pressure increases with blood aspiration, filtration correspondingly increases.

Aspirated blood is admixed with washing fluid aspirated from the washing fluid bag 130 in suction tubing 114. Admixed blood/washing fluid is filtered through the emboli filter 118, and is then carried through the conduit 139. The conduit 139 is fitted with bubble traps 232, 234 to allow the venting off of any residual bubbles which, when trapped in the blood column in the conduit 139, decrease or prevent the flow of blood in the column.

Though the blood may be filtered through the membrane filter 138 in a single pass, the blood may be further filtered by causing blood collected in the blood collection bag 170 to flow into the reservoir bag 224 associated with the conduit 139. Blood may be made to flow from the blood collection bag 170 into the reservoir bag 224 by sequentially producing negative pressure and positive (atmospheric) pressure in the blood collection bag 170. Manipulation of negative and positive pressure in the blood collection bag 170 is accomplished by manipulating the two-way valve 212 associated with the blood collection bag 170; the two-way valve 212 operates to either allow vacuum suction to be applied to the blood collection bag 170, or to introduce atmospheric pressure into the blood collection bag 170. As alternating negative and positive pressure is applied to the blood collection bag 170, blood is caused to circulate between the blood circulation bag and the reservoir bag 224. Filtration occurs with every pass through the membrane filter 138. Two blood collection bags are provided so that one may become full, and reinfusion can take place from that blood collection bag 170 while the other blood collection bag 214 (or stand-by bag) continues to fill with filtered blood. Infusion from the blood collection bag takes place when an infusion line is attached to the infusion port 176 of the blood collection bag 170, the clamp 216 attached to the second conduit 141 below the blood collection bag 170 is secured in the closed position, and atmospheric pressure is introduced into the bag by engaging the two-way valve 212 in the open position. Infusion then takes place by gravity flow. At the same time, the clamp 218 on the second conduit 141 leading to the stand-by blood collection bag 214 is opened to allow blood to collect therein. Negative pressure is applied to the blood collection bag 214 by engaging the two-way valve 220 to open to the vent line 210 of the vacuum source 128.

The various embodiments of the invention provide membrane filtration systems for both intraoperative and post-surgical applications, which operate continuously on-line, on a real time basis, providing washing fluid in proportion to bleeding rate, filtration to remove particulates larger than 40 micron, and membrane filtration to remove washing fluid, and other impurities which are below a desired molecular size. Most importantly, the present invention provides to the patient, in some embodiments, his/her own purified blood at the required hematocrit value free of air emboli at the same rate at which it is lost from the wound site.

The embodiments shown in the figures, along with the descriptions thereof, are by way of illustration and are not intended to limit the possible configurations of the invention or to limit the scope of the invention as claimed below.

What is claimed is:

1. An apparatus for filtering autologous blood taken from a patient for reinfusion to the patient comprising:
   suction means for aspirating blood from a wound site;
   first conduit means for conducting said aspirated blood from said suction means;
   washing fluid retainer means for retaining washing fluid for admixing with said aspirated blood;
   second conduit means interconnected between said washing fluid retainer means and said first conduit for conducting washing fluid therebetween;
   first filter means for removing emboli and large particulates from said aspirated blood, said first filter means being connected to said first conduit means;
   filter casing means for enclosing said first filter means therein, said filter casing having vacuum connector means associated therewith for attaching a source of vacuum;
   reservoir means associated with said filter casing means for collecting filtered blood from said first filter means;
   second filter means for filtering excess fluids and impurities from said blood;
   third conduit means interconnected between said reservoir means and said second filter means for conducting blood therebetween;
   blood collection means for collecting filtered blood;
   fourth conduit means interconnected between said second filter and said blood collection means for conducting filtered blood therebetween;
   filtrate container means for containing said excess fluids and impurities filtered from said blood by said second filter means;
   fifth conduit means interconnected between said second filter means and said filtrate container means for conducting filtrate therethrough; and
   reinfusion means associated with said blood collection means for reinfusing purified blood to the patient.

2. The apparatus of claim 1 wherein said washing fluid retainer means is positioned below said suction means.

3. The apparatus of claim 2 wherein said first filter means is positioned from about two feet to about five feet above the relative height of said suction means.

4. The apparatus of claim 3 wherein said first filter means is positioned relative to said second filter means to enable movement of blood to the latter by gravity.

5. The apparatus of claim 4 wherein said blood collection means is positioned at a height above the relative height of said second filter means.

6. The apparatus of claim 5 wherein said filtrate container means has vacuum connector means associated therewith.

7. The apparatus of claim 6 further comprising adjustable clamp means associated with said first conduit for closing off said first conduit.

8. The apparatus of claim 6 wherein said blood collection means comprises a plurality of non-collapsible containers, each container having associated therewith a vacuum connector means for attaching a source of vacuum.

9. The apparatus of claim 8 wherein said fourth conduit is divided into separate branches, each said separate branch of said fourth conduit being attachable to a said non-collapsible container.

10. The apparatus of claim 9 further comprising vacuum line means associated with each said vacuum connector means of each said non-collapsible container and further associated with said vacuum connector means of said filter casing, said vacuum line being attachable to a vacuum source.

11. The apparatus of claim 10 further comprising vacuum control means associated with said vacuum line to control the amount of pressure applied to each said non-collapsible container by the vacuum source.

12. The apparatus of claim 11 further comprising filter means attached to said vacuum line associated with each said non-collapsible container for filtering and preventing unwanted particles from entering said non-collapsible containers through said vacuum line.

13. The apparatus of claim 12 wherein said vacuum line is also connected to said vacuum connector means of said filtrate container.

14. The apparatus of claim 13 further comprising air venting means for venting off entrapped air bubbles from the blood, said air venting means being interconnected between said third conduit and said filter casing means.

15. The apparatus of claim 14 further comprising auxiliary blood collection means connected to said third conduit means for collecting blood therein, said auxiliary blood collection means having port means for conducting fluids therethrough.

16. The apparatus of claim 5 further comprising first blood level detector means associated with said blood collection means for detecting the level of blood in said blood collection means.

17. The apparatus of claim 16 further comprising second blood component level detector means associated with said reinfusion means for measuring the level of blood components in said blood prior to reinfusion.

18. The apparatus of claim 17 further comprising anticoagulant neutralizer container means connected to said reinfusion means for retaining anticoagulant neutralizer.

19. The apparatus of claim 18 further comprising first pump means connected to said reinfusion means for pumping blood from said blood collection means to said patient.

20. The apparatus of claim 19 further comprising second pump means connected to said fifth conduit for urging said filtrate from said second filter means.

21. The apparatus of claim 20 further comprising control means in electro-mechanical communication with said adjustable clamp means associated with said first conduit means for actuating said clamp means.

22. The apparatus of claim 1 wherein said first filter further comprises porous material having a pore size of about 40 microns and having an upper end and a lower end, said lower end being covered with hydrophilic fabric and said upper end being covered with hydrophobic fabric, and said porous material being contacted with an antifoam agent.

23. The apparatus of claim 1 wherein said second filter comprises a porous membrane having a pore size from about 40,000 daltons to about 0.4 microns.

24. The apparatus of claim 23 wherein said pore size of said porous membrane is about 100,000 daltons.

25. The apparatus of claim 1 wherein said suction means further comprises:
   handle means for grasping;
   first duct means for passage of blood therethrough, said first duct means having a first end defining a tip and a second end for connection to said first conduit means;
   second duct means for passage of washing fluid therethrough, said second duct having a first opening in communication with said second conduit means and a second opening in communication with said first duct means such that said first duct means and said second duct means are substantially parallel and the movement of said blood through said fist duct means and the movement of said washing fluid in said second duct means is in the same direction.

26. An apparatus for filtering autologous blood taken from a patient for reinfusion to the patient comprising:
   suction means for aspirating blood from a wound site;
   first conduit means for conducting said aspirated blood from said suction means;
   first filter means for removing emboli and large particulates from said aspirated blood, said first filter means being connected to said first conduit means;
   filter casing means for enclosing said first filter means therein, said filter casing having vacuum connector means associated therewith for attaching a source of vacuum;
   reservoir means associated with said filter casing means for collecting filtered blood from said first filter means;
   second filter means for filtering excess fluids and impurities from said blood;
   second conduit means interconnected between said reservoir means and said second filter means for conducting blood therebetween;
   blood collection means for collecting filtered blood;
   third conduit means interconnected between said second filter and said blood collection means for conducting filtered blood therebetween;
   filtrate container means for containing said excess fluids and impurities filtered from said blood by said second filter means;
   fourth conduit means interconnected between said second filter means and said filtrate container means for conducting filtrate therethrough;
   first adjustable clamp means associated with said fourth conduit means for preventing flow of filtrate therethrough; and
   reinfusion means associated with said blood collection means for reinfusing purified blood to the patient.

27. The apparatus of claim 26 wherein said third conduit further comprises separate branches, each branch having connector means for attaching blood collection means thereto.

28. The apparatus of claim 27 wherein each said blood collection means has a port means for passage of fluids therethrough.

29. The apparatus of claim 26 further comprising auxiliary blood retainer means connected to said second conduit means for retaining blood conducted through said second conduit from said reservoir, and further comprising second adjustable clamp means associated with said second conduit means between said auxiliary blood retainer means and said second filter means for preventing fluid from passing therebetween.

30. The apparatus of claim 29 wherein said auxiliary blood retainer means has port means for passage of fluid therethrough.

31. The apparatus of claim 30 wherein said blood collection means contains washing fluid therein for mixing with said aspirated blood.

32. The apparatus of claim 31 wherein said suction means is positioned from about two feet to about five feet below the relative height of said first filter means, wherein said first filter means is at least six feet in height above said second filter means, and wherein said second conduit means is at least six feet in length.

33. The apparatus of claim 32 further comprising vacuum regulator means in communication with said first filter means for regulating the amount of negative pressure applied thereto.

34. The apparatus of claim 33 wherein said vacuum regulator means is a water manometer.

35. The apparatus of claim 34 further comprising bifurcated vacuum line means for attachment to a vacuum source, one end of said bifurcated vacuum line means being connected to said vacuum connector means of said filter casing means and the other end of said bifurcated vacuum line means being attached to said water manometer.

36. The apparatus of claim 35 wherein said bifurcated vacuum line has first valve means connected thereto, in proximity to said filter casing means, for preventing flow of liquid into said vacuum line means, and further comprising vacuum monitor means associated with said bifurcated vacuum line means for monitoring the pressure supplied by said vacuum source.

37. The apparatus of claim 36 further comprising valve means attached to said first conduit means for preventing backflow of matter therethrough.

38. The apparatus of claim 37 further comprising third adjustable clamp means connected to said second conduit means between said first filter means and said auxiliary blood retainer means for preventing passage of blood therethrough.

39. The apparatus of claim 33 wherein said vacuum regulator means is a piston-type regulator.

40. The apparatus of claim 32 further comprising vacuum connector means associated with said filtrate container means for attachment of a source of vacuum.

41. The apparatus of claim 26 wherein said first filter further comprises porous material having a pore size of about 40 microns and having an upper end and a lower end, said lower end being covered with hydrophilic fabric and said upper end being covered with hydrophilic fabric, and said porous material being contacted with an antifoam agent.

42. The apparatus of claim 26 wherein said second filter comprises a porous membrane having a pore size from about 40,000 daltons to about 0.4 microns.

43. The apparatus of claim 42 wherein said pore size of said porous membrane is about 100,000 daltons.

44. An apparatus for filtering autologous blood taken from a patient for reinfusion to the patient comprising:
   suction means for aspirating blood from a wound site;

first conduit means for conducting said aspirated blood from said suction means;

washing fluid retainer means for retaining washing fluid for admixing with said aspirated blood;

second conduit means interconnected between said washing fluid retainer means and said first conduit for conducting washing fluid therebetween;

first filter means for removing emboli and large particulates from said aspirated blood, said first filter means being connected to said first conduit means;

filter casing means for enclosing said first filter means therein, said filter casing having vacuum connector means associated therewith for attaching a source of vacuum;

reservoir means associated with said filter casing means for collecting filtered blood from said first filter means;

second filter means for filtering excess fluids and impurities from said blood, said second filter being in communication with said filter casing means;

filtrate container means for containing said excess fluids and impurities filtered from said blood by said second filter means;

third conduit means interconnected between said second filter means and said filtrate container means for conducting filtrate therethrough; and fourth conduit means in communication with said reservoir means for conducting filtered blood therethrough for reinfusion.

45. The apparatus of claim 44 wherein said first filter means and said second filter means are conjoined into said filter casing means, and further comprising vacuum connector means associated with said filter casing means for attaching a source of vacuum.

46. The apparatus of claim 45 further comprising first pump means associated with said third conduit means for urging said filtrate therethrough, second pump means associated with said fourth conduit means for urging filtered blood therethrough, and blood level detector means connected to said reservoir means for detecting the level of blood therein.

47. The apparatus of claim 46 further comprising blood component detector means connected to said fourth conduit means for detecting blood component levels in blood passing therethrough.

48. The apparatus of claim 46 further comprising third pump means associated with said second conduit for urging washing fluid therethrough.

49. The apparatus of claim 48 wherein said first pump means, said second pump means, and said third pump means are in electromechanical communication with each other.

50. The apparatus of claim 49 further comprising vent pump means associated with said filter casing means for venting air from said filter casing means and first filter means, and further comprising pressure regulator means connected to said filter casing means for regulating pressure thereto.

51. The apparatus of claim 44 further comprising fifth conduit means interconnected between said reservoir means and said second filter means for conducting blood therebetween, and further comprising recirculation pump means associated with said fifth conduit for urging blood therethrough.

52. The apparatus of claim 51 further comprising sixth conduit means interconnected between said second filter means and said reservoir means for conducting blood therethrough, said sixth conduit means being in communication with said fourth conduit means.

53. The apparatus of claim 52 further comprising blood level detector means associated with said reservoir means for measuring high and low levels of blood in said reservoir means.

54. The apparatus of claim 53 further comprising flow constriction means associated with said second filter means for providing transmembrane pressure in said second filter.

55. The apparatus of claim 54 further comprising blood component level detector means connected to said sixth conduit means for measuring the level of blood components in said blood.

56. The apparatus of claim 55 further comprising first valve means connected to said fourth conduit means and said sixth conduit means for alternately directing blood through said sixth conduit means and said fourth conduit means.

57. The apparatus of claim 56 further comprising second valve means connected to said third conduit means for opening and closing said conduit means.

58. The apparatus of claim 57 wherein said first valve means, said second valve means, said recirculation pump means and said blood component level detector means are in electromechanical communication with each other.

59. The apparatus of claim 58 further comprising third filter means connected to said fourth conduit means for filtering emboli and residual impurities from the blood prior to infusion, said filter having blood level detector means connected thereto for measuring the level of blood in said third filter means, and further comprising third valve means connected to said fourth conduit means for closing said fourth conduit, said third valve means being in electromechanical communication with said blood level detector means of said third filter means, said blood level detector means of said reservoir means, and said blood component level detector means.

60. The apparatus of claim 44 wherein said suction means further comprises:

handle means for grasping;

first duct means for passage of blood therethrough, said first duct means having a first end defining a tip and a second end for connection to said first conduit means;

second duct means for passage of washing fluid therethrough, said second duct having a first opening in communication with said second conduit means and a second opening in communication with said first duct means such that said first duct means and said second duct means are substantially parallel and the movement of said blood through said fist duct means and the movement of said washing fluid in said second duct means is in the same direction.

61. A method of recycling autologous blood for reinfusion into a patient comprising:

aspirating an amount of blood from a wound site under vacuum pressure;

admixing said blood with an amount of washing fluid approximately proportional to that of said blood;

introducing said admixture of approximately proportional amounts of blood and washing fluid into a first emboli filter under vacuum pressure;

filtering said admixture of blood and washing fluid through said emboli filter to remove air and large particles;

filtering said admixture through a membrane filter to remove impurities and excess fluid; and reinfusing said filtered blood into said patient.

62. The method according to claim 61 further comprising monitoring said blood for volume of cellular components in said blood after filtering said blood through said membrane filter.

63. The method according to claim 62 further comprising recirculating said blood through said membrane filter and said emboli filter prior to reinfusing said blood into said patient until a desired amount of excess fluid and impurities have been removed, and a desired volume of blood cellular components remain in said blood.

64. The method according to claim 63 further comprising filtering said blood through a second emboli filter prior to reinfusing said blood into said patient to remove any air emboli and impurities therefrom.

* * * * *